(12) United States Patent
Coy

(10) Patent No.: US 8,216,792 B2
(45) Date of Patent: Jul. 10, 2012

(54) COMPOSITIONS AND METHODS FOR DETECTION AND TREATMENT OF PROLIFERATIVE ABNORMALITIES ASSOCIATED WITH OVEREXPRESSION OF HUMAN TRANSKETOLASE LIKE-1 GENE

(76) Inventor: Johannes Coy, Grossostheim (DE)

( * ) Notice: Subject to any disclaimer, the term of this patent is extended or adjusted under 35 U.S.C. 154(b) by 193 days.

(21) Appl. No.: 12/615,592

(22) Filed: Nov. 10, 2009

(65) Prior Publication Data

US 2010/0136577 A1  Jun. 3, 2010

Related U.S. Application Data

(62) Division of application No. 10/511,813, filed as application No. PCT/EP03/03827 on Apr. 12, 2003, now Pat. No. 7,655,398.

(30) Foreign Application Priority Data

Apr. 19, 2002  (EP) .................................... 02008831

(51) Int. Cl.
*G01N 33/53* (2006.01)
(52) U.S. Cl. ....................................................... 435/7.1
(58) Field of Classification Search .................. None
See application file for complete search history.

(56) References Cited

FOREIGN PATENT DOCUMENTS

| WO | 97/05253 A | 2/1997 |
|---|---|---|
| WO | 98/53319 A | 11/1998 |
| WO | 00/52204 A | 9/2000 |

OTHER PUBLICATIONS

Tockman et al (Cancer Res., 1992, 52:2711s-2718s).*
Langbein, et al; "Expression of Transketolase TKTLI Predicts Colon and Urothelial Cancer Patient Survival: Warburg Effect Reinterpreted"; British Journal of Cancer, 2006; 94(4); pp: 578-585.
Coy, J, et al; "Molecular Cloning of Tissue-Specific Transcripts of a Transketolase-Related Gene: Implications for the Evalustion of New Vertebrate Genes"; Genomics; Academic Press, San diego, US, vol. 32; No. 3 ; pp. 309-316; 1996 XP000616489 ISSN: 0888-7543.
Cascante, M., et al; "Role of Thiamin (Vitamin B-1) and Transketolase in Tumor Cell Proliferation"; Nutrition and Cancer; vol. 36, No. 2; 2000; pp. 150-154 XP008012308.
Spentzos, et al; "Transketolase Gene Expression May Be a marker of Sensitivity to Platinum/Paclitaxel Chemotherapy in Ovarian Cancer"; Procedings of the American Association for Cancer Research Annual Meeting; vol. 43; Mar. 2002; pp. 1105-1106 XP008012309.
Lynch, H, et al; "Hereditary Cancer: Family History, Diagnosis, Molecular Genetics, Ecogenetics, and Management Strategies"; Biochemie; vol. 84; No. 1; Jan. 2002; pp. 3-17 XP001148125.

\* cited by examiner

*Primary Examiner* — Sean Aeder
(74) *Attorney, Agent, or Firm* — Joyce von Natzmer; Agris & von Natzmer LLP

(57) ABSTRACT

Methods for in vitro diagnosis of carcinoma are disclosed. In one aspect the invention relates to methods such as detecting the level of transketolase like-1 polypeptide, which are especially useful for the detection of tumors and their precursory stages based on the detection of overexpression of human transketolase like-1 gene in biological samples. In another aspect the invention relates to methods for treatment of disorders associated with the overexpression of human transketolase like-1 gene. Methods for treatment may include gene therapeutic approaches as well as methods for inhibiting or reducing the activity of transketolase like-1 polypeptides.

41 Claims, 12 Drawing Sheets

TKT-L1

TKT-L1

TKT-L1

TKT

TKT

TKT

Fig. 7: DNA and amino acid sequence of TKT-L1

```
   1  GCCATTCGCTCTTCAGACGCCGGAGACGTAGGAGTGGGTCTTCAGACTCCAAAGGGGTTG

61  GACTAATGGCGGATGCTGAGGCGAGGGCTGAGTTCCCGGAGGAGGCCAGACCTGACAGGG
         M  A  D  A  E  A  R  A  E  F  P  E  E  A  R  P  D  R  G

121  GCACCTTGCAGGTGTTGCAAGATATGGCCAGCCGCTTGCGAATCCATTCCATCAGGGCCA
       T  L  Q  V  L  Q  D  M  A  S  R  L  R  I  H  S  I  R  A  T

181  CATGCTCCACGAGCTCCGGCCACCCTACATCATGTAGCAGTTCTTCTGAGATCATGTCTG
        C  S  T  S  S  G  H  P  T  S  C  S  S  S  E  I  M  S  V

241  TGCTGTTCTTCTACATCATGAGGTACAAGCAGTCAGATCCAGAGAATCCGGACAACGACC
        L  F  F  Y  I  M  R  Y  K  Q  S  D  P  E  N  P  D  N  D  R

301  GATTTGTCCTCGCAAAGAGACTGTCGTTTGTGGATGTGGCAACAGGATGGCTCGGACAAG
         F  V  L  A  K  R  L  S  F  V  D  V  A  T  G  W  L  G  Q  G

361  GACTGGGAGTTGCATGTGGAATGGCATATACTGGCAAGTACTTCGACAGGGCCAGCTACC
         L  G  V  A  C  G  M  A  Y  T  G  K  Y  F  D  R  A  S  Y  R

421  GGGTGTTCTGCCTCATGAGTGATGGCGAGTCCTCAGAAGGCTCTGTCTGGGAGGCAATGG
         V  F  C  L  M  S  D  G  E  S  S  E  G  S  V  W  E  A  M  A

481  CCTTTGCTTCCTACTACAGTCTGGACAATCTTGTGGCAATCTTTGATGTGAACCGCCTGG
         F  A  S  Y  Y  S  L  D  N  L  V  A  I  F  D  V  N  R  L  G

541  GACACAGTGGTGCATTGCCCGCCGAGCACTGCATAAACATCTATCAGAGGCGCTGCGAAG
         H  S  G  A  L  P  A  E  H  C  I  N  I  Y  Q  R  R  C  E  A

601  CCTTTGGGTGGAACACTTATGTGGTGGACGGCCGGGACGTGGAGGCACTGTGCCAGGTAT
         F  G  W  N  T  Y  V  V  D  G  R  D  V  E  A  L  C  Q  V  F

661  TCTGGCAGGCTTCTCAGGTGAAGCACAAGCCCACTGCTGTGGTGGCCAAGACCTTCAAGG
         W  Q  A  S  Q  V  K  H  K  P  T  A  V  V  A  K  T  F  K  G

721  GCCGGGGCACCCCAAGTATTGAGGATGCAGAAAGTTGGCATGCAAAGCCAATGCCAGAGAG
         R  G  T  P  S  I  E  D  A  E  S  W  H  A  K  P  M  P  R  E

781  AAAGAGCAGATGCCATTATCAAATTAATTGAGAGCCAGATACAGACCAGCAGGAATCTTG
         R  A  D  A  I  I  K  L  I  E  S  Q  I  Q  T  S  R  N  L  D

841  ACCCACAGCCCCCCATTGAGGACTCACCTGAAGTCAACATCACAGATGTAAGGATGACCT
         P  Q  P  P  I  E  D  S  P  E  V  N  I  T  D  V  R  M  T  S

901  CTCCACCTGATTACAGAGTTGGTGACAAGATAGCTACTCGGAAAGCATGCGGTCTGGCTC
         P  P  D  Y  R  V  G  D  K  I  A  T  R  K  A  C  G  L  A  L

961  TGGCTAAGCTGGGCTACGCGAACAACAGAGTCGTTGTGCTGGATGGTGACACCAGGTACT
         A  K  L  G  Y  A  N  N  R  V  V  V  L  D  G  D  T  R  Y  S

1021  CTACTTTCTCTGAGATATTCAACAAGGAGTACCCTGAGCGCTTCATCGAGTGCTTTATGG
         T  F  S  E  I  F  N  K  E  Y  P  E  R  F  I  E  C  F  M  A

1081  CTGAACAAAACATGGTGAGCGTGGCTCTGGGCTGTGCCTCCCGTGGACGGACCATTGCTT
         E  Q  N  M  V  S  V  A  L  G  C  A  S  R  G  R  T  I  A  F

1141  TTGCTAGCACCTTTGCTGCCTTTCTGACTCGAGCATTTGATCACATCCGGATAGGAGGCC
         A  S  T  F  A  A  F  L  T  R  A  F  D  H  I  R  I  G  G  L
```

Fig. 7 Continued

```
1201  TCGCTGAGAGCAACATCAACATTATTGGTTCCCACTGTGGGGTATCTGTTGGTGACGATG
       A  E  S  N  I  N  I  I  G  S  H  C  G  V  S  V  G  D  D  G

1261  GTGCTTCCCAGATGGCCCTGGAGGATATAGCCATGTTCCGAACCATTCCCAAGTGCACGA
       A  S  Q  M  A  L  E  D  I  A  M  F  R  T  I  P  K  C  T  I

1321  TCTTCTACCCAACTGATGCCGTCTCCACGGAGCATGCTGTTGCTCTGGCAGCCAATGCCA
       F  Y  P  T  D  A  V  S  T  E  H  A  V  A  L  A  A  N  A  K

1381  AGGGGATGTGCTTCATTCGGACCACCCGACCAGAAACTATGGTTATTTACACCCCACAAG
       G  M  C  F  I  R  T  T  R  P  E  T  M  V  I  Y  T  P  Q  E

1441  AACGCTTTGAGATCGGACAGGCCAAGGTCCTCCGCCACTGTGTCAGTGACAAGGTCACAG
       R  F  E  I  G  Q  A  K  V  L  R  H  C  V  S  D  K  V  T  V

1501  TTATTGGAGCTGGAATTACTGTGTATGAAGCCTTAGCAGCTGCTGATGAGCTTTCGAAAC
       I  G  A  G  I  T  V  Y  E  A  L  A  A  A  D  E  L  S  K  Q

1561  AAGATATTTTTATCCGTGTCATCGACCTGTTTACCATTAAACCTCTGGATGTCGCCACCA
       D  I  F  I  R  V  I  D  L  F  T  I  K  P  L  D  V  A  T  I

1621  TCGTCTCCAGTGCAAAAGCCACAGAGGGCCGGATCATTACAGTGGAGGATCACTACCCGC
       V  S  S  A  K  A  T  E  G  R  I  I  T  V  E  D  H  Y  P  Q

1681  AAGGTGGCATCGGGGAAGCTGTCTGCGCAGCCGTCTCCATGGATCCTGACATTCAGGTTC
       G  G  I  G  E  A  V  C  A  A  V  S  M  D  P  D  I  Q  V  H

1741  ATTCGCTGGCAGTGTCGGGAGTGCCCCAGAGTGGGAAGTCCGAGGAATTGCTGGATATGT
       S  L  A  V  S  G  V  P  Q  S  G  K  S  E  E  L  L  D  M  Y

1801  ATGGAATTAGTGCCAGACATATCATAGTGGCCGTGAAATGCATGTTGCTGAACTAAAATA
       G  I  S  A  R  H  I  I  V  A  V  K  C  M  L  L  N  *

1861  GCTGTTAGCCTTGGTCTTTTGGCCTCTTTACCCTGTGTTTATGTTTGTTCCAAAACCATC

1921  ATTTAAATCTCTACTGTCACATTTTGTTTCTTAAAAGCAAAGCCAGCTAACACCTTCATT

1981  CATCCCTAGTTCGGAAATTCAAGCTAACTACTTACCCTTTAAACTGTCACTGCATATGCA

2041  AGTACCGCTCTAATTTTTGGATCATTAAAGGGAGTTACACAACTTTTAAGTGAAAAAAAT

2101  AGGTAACAAAACAACCACCTGATAGTAAGTTTTCTGATAAGACTATAGATAAGTGGTAGA

2161  GGTAATCAATTCTTCCGAAGTGTTTCCTTCGTGAATAACTGGTAGAGGTAATAGTTTTTT

2221  CAATGTATTTCCTTCATGAGTAAAGAAAATGTGGATTGAAGTATAGATTCCAGTAGCCTA

2281  GTTTCCACAGCACGATAACACCATGACGCCTACTGCTGTTCCCACCTTGGGATTCTGTGT

2341  GCTGCCATCCCACCTGCAGCTGCCCTGGAATTCCCTTCGCTGTTTGCCTTCATCTCCCTC

2401  CACGTTTGAGAGGCTGTCAGGCAGCAGCGAAAGCTTGTTAGGATGTCCTGTGCTGCTTGT

2461  GATGAGAGCCTCCACACTGTACTGTTCAAGTCAATGTTAATAAAGCATTTCAAAACCAAA

2521  AAAAAAAAAAA
```

Fig. 8
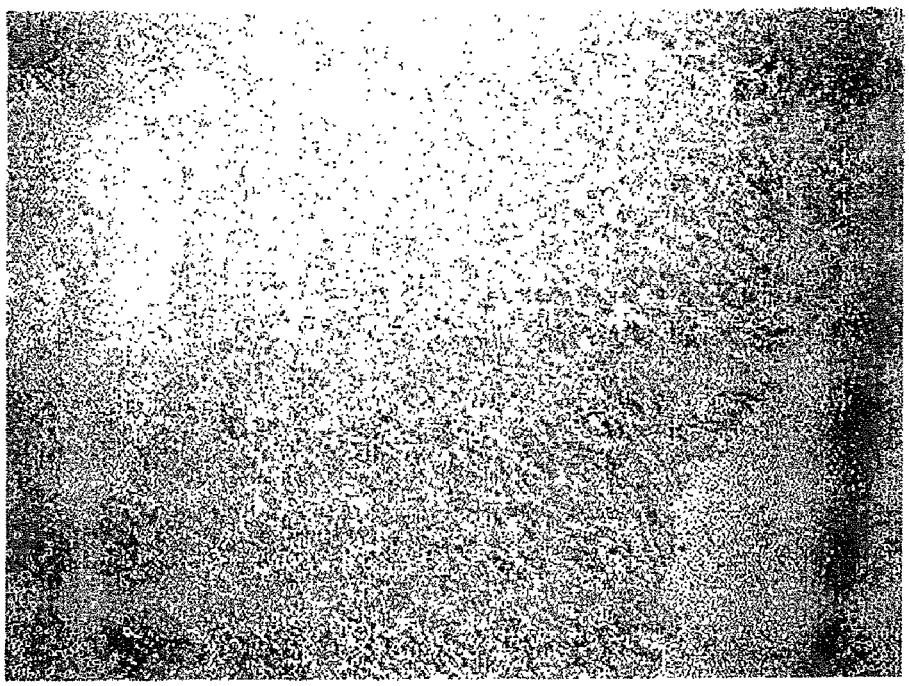
A  1666
B  1666

Fig.9
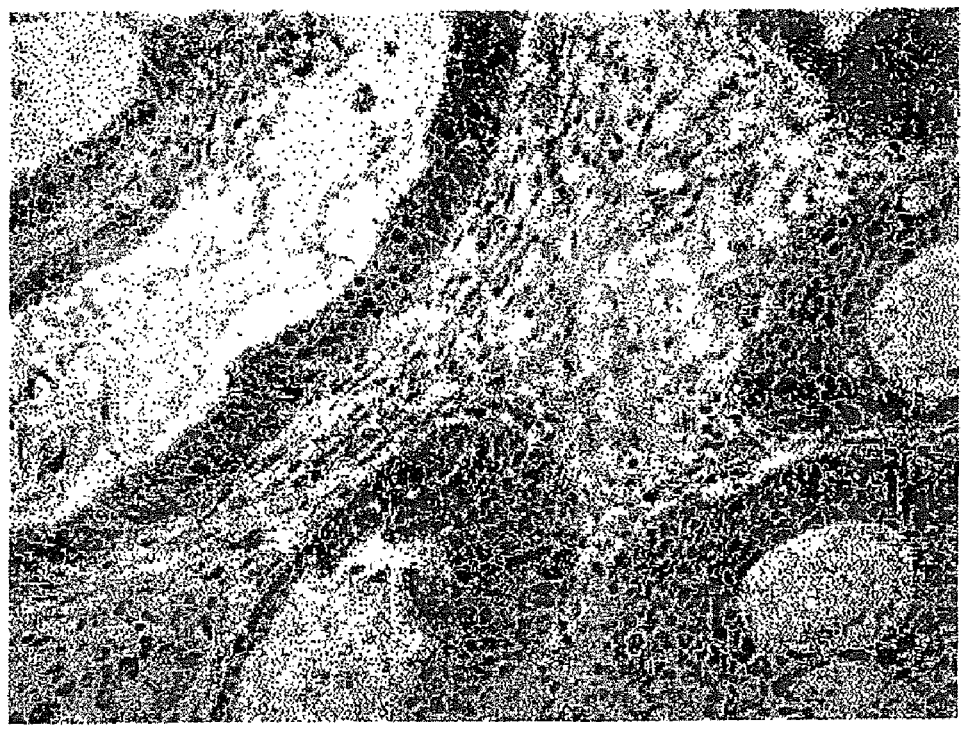
A          1682
B          1697

Fig.10
A       1699
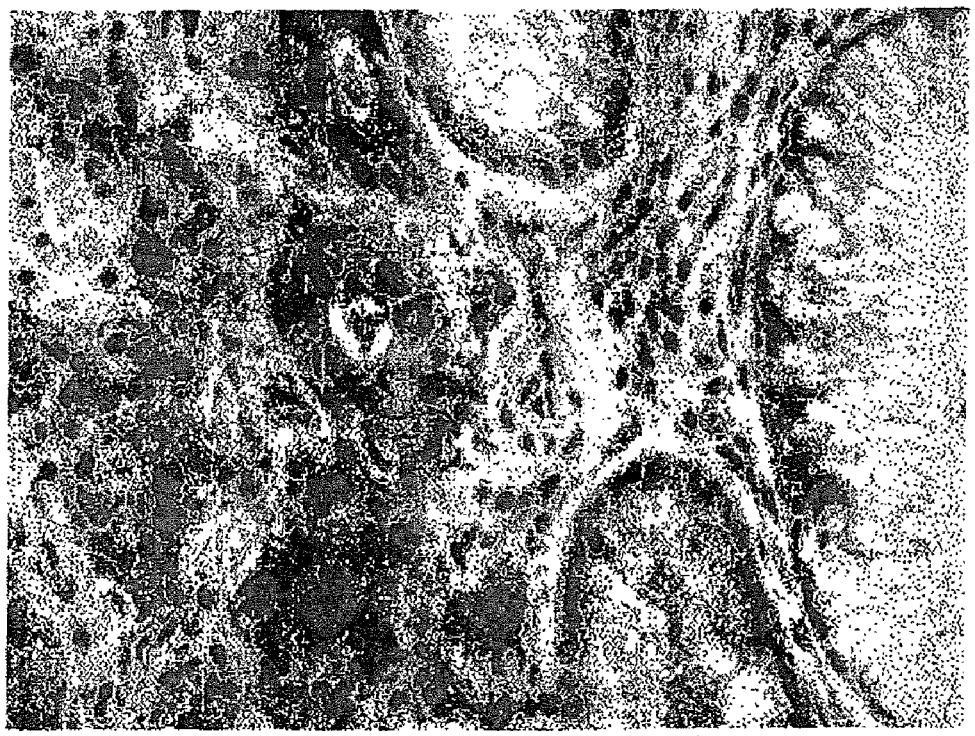
B       1699

Fig. 11
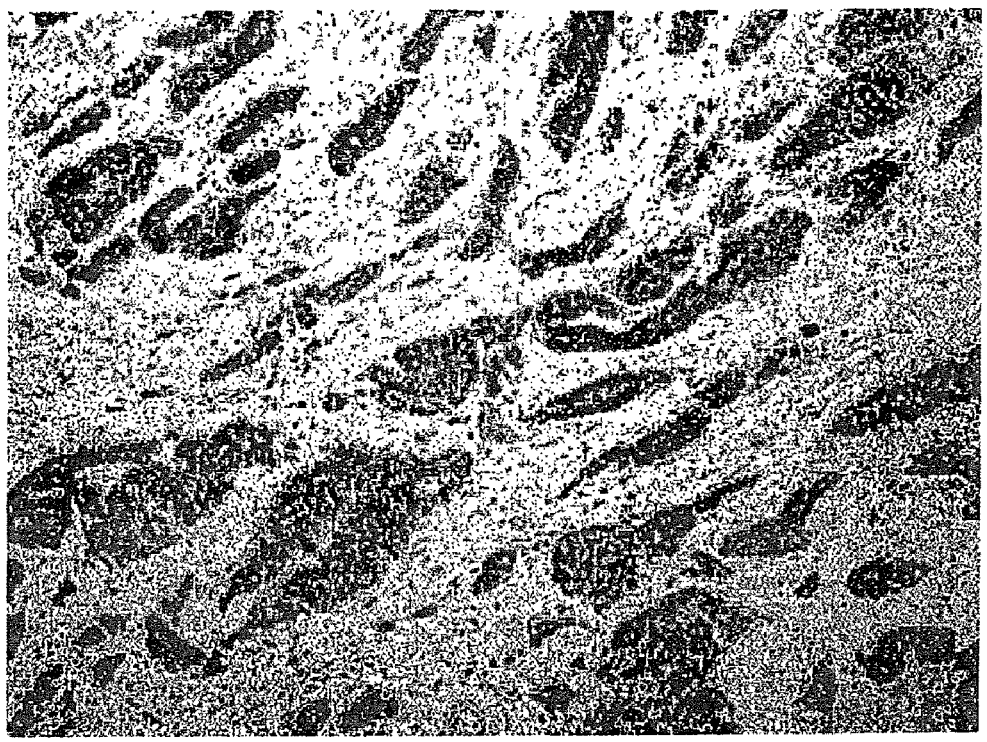
A    1698
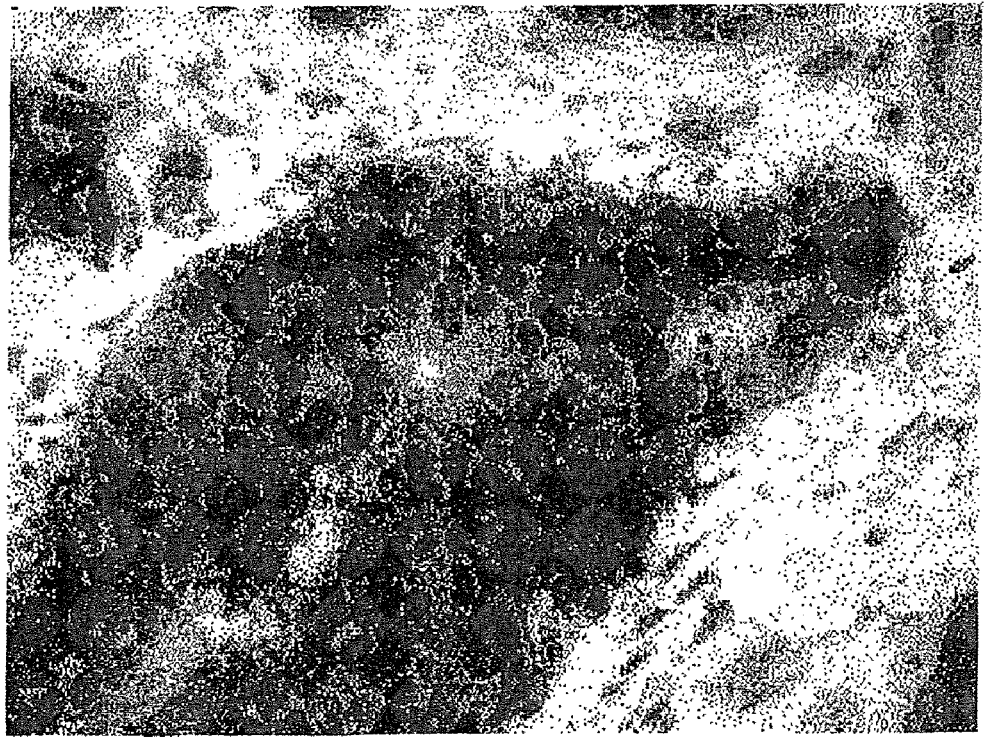
B    1698

COMPOSITIONS AND METHODS FOR DETECTION AND TREATMENT OF PROLIFERATIVE ABNORMALITIES ASSOCIATED WITH OVEREXPRESSION OF HUMAN TRANSKETOLASE LIKE-1 GENE

The present invention relates to methods for treatment and diagnosis of disorders associated with abnormally proliferating cells. In one aspect the invention relates to methods, which are especially useful for the detection of tumors and their precursory stages based on the detection of overexpression of human transketolase like-1 gene in biological samples. In another aspect the invention relates to methods for treatment of disorders associated with the overexpression of human transketolase like-1 gene. Methods for treatment may include gene therapeutic approaches as well as methods for inhibiting or reducing the activity of transketolase like-1 polypeptides.

Despite significant scientific and medical research efforts, neoplastic diseases still remain a major cause of human mortality. For example each year more than 340,000 persons in Germany develop cancer and more than 210,000 die from their disease. Epithelial tumors represent the majority of cancer: Lung cancer is the leading cause of cancer deaths in males, and breast cancer is the leading cause in females. The second leading cause of cancer deaths for both sexes is colorectal cancer (Becker, N. and Wahrendorf, J., (1997) Atlas of Cancer Mortality in the Federal republic of Germany 1981-1990, Springer-Verlag, Berlin, Heidelberg).

One major reason for this unsatisfying situation is, that most neoplastic diseases are diagnosed at relatively late stages, when isolated tumor cells or small tumor cell aggregates were already released from the primary tumor and distributed in the whole organism of the host and might have eventually already caused occult or frank metastatic disease. Early cancers and in particular precancers usually do not cause any symptoms and are not realized by the respective patients.

To overcome this, more research efforts and clinical programs are required to improve cancer early detection technologies, as well as to develop true preventive or therapeutic vaccination strategies to immunize patients either before a defined cancer emerged or after resection of a cancer or its precursors to prevent survival of disseminated isolated cancer cells (DTCs) which might have been released from the neoplasm either before or during primary surgical intervention.

For few cancers, in particular cancer of the uterine cervix efficient cancer early detection programs could be established. The subsequent reduction of mortality rates associated with these specific neoplasms convincingly demonstrated the high effectiveness of the early detection programs.

To summarize, unfortunately, the diagnostic methods used so far are relatively insensitive and take the risk to yield false-positive results due to lack of specificity. Moreover, by using the current diagnostic methods any conclusions as regards the grade of malignancy, the progression of the tumor and its potential for metastasising cannot be precisely predicted.

Thus, the use of reliable diagnostic molecular markers would be highly beneficial for an understanding of the molecular basis of epithelial tumors, e.g. colon tumors, for distinguishing benign from malignant tissue and for grading and staging carcinomas, particularly for patients with metastasising cancer having a very bad prognosis. It can be expected that such markers are also useful for the development of novel therapeutic avenues for cancer treatment.

The understanding of the molecular events underlying the transition of a normal cell into a tumor cell of different grades of aggressiveness and the availability of appropriate experimental systems to select for cancer-associated genes are absolute prerequisites for the identification of such novel diagnostic markers and therapeutic drug targets.

It is commonly accepted that tumorigenesis represents a complex multistage process in which genetic changes and environmental factors are thought to deregulate the cellular processes that control cell proliferation and differentiation. This multistep process is well illustrated for example by colorectal cancers, which typically develop over decades and appear to require multiple genetic events for completion (for review Kinzler and Vogelstein, 1996, Cell 87, 159-170). Both inheritance of altered genes (resulting in a marked predisposition) and genomic instability (caused by genotoxic agents from the environment) resulting in additional somatic mutations contribute to this process. Clearly, the list of decisive players causally involved in tumor formation is far from being complete and will obviously vary depending on the type of tumor.

Thus, the technical problem underlying the present invention is to provide means for diagnosis and therapy of epithelial tumors, which overcome the disadvantages of the presently available diagnostic and therapeutic methods.

The solution to said technical problem is achieved by providing the embodiments characterized in the claims.

The present invention is based on the inventors findings, that human transketolase like-1 gene as given in SEQ. ID. 1 (cf. TKT-L1, TKR: NM_012253; Accession number: X91817) is highly overexpressed in tissue of colon carcinoma, pancreatic carcinoma, lung cancer and gastric cancer compared to the level found in respective normal control tissue. This is especially valuable for diagnostic purposes, as transketolase enzyme is not comparably overexpressed in tumour tissue.

Thus a method for diagnosis of tumors can be based on the detection of overexpression of transketolase like-1 gene products in biological samples. According to the detected presence or absence and/or level of transketolase like-1 gene products it is possible to predict the disease course, to assess prognosis and to tailor adequate therapy for patients.

Furthermore the invention enables for therapeutic methods applicable to disorders associated with the overexpression of transketolase like-1 gene products. On the one hand the invention provides methods using transketolase like-1 nucleic acids or polypeptides for the therapy of disorders. On the other hand the invention provides for methods based on the reduction of the enzymatic activity of transketolase like-1 gene polypeptides. Thus it is one aspect of the invention to provide a method for rational tumor management based on the detection of transketolase like-1 gene products in patient samples and the tailoring of a therapy correlated to the detected overexpression of said gene products.

Finally the present invention relates to diagnostic and research kits and to pharmaceutical compositions useful for performing the methods disclosed herein.

BRIEF DESCRIPTION OF THE DRAWINGS

FIG. 7: DNA and amino acid sequence of tktl1; the part of the protein being used for the immunization for antibody generation is given in bold letters; additionally peptides are underlined which were used for peptide immunization for antibody generation.

FIG. 8: Immunohistochemical analysis of gastric carcinoma (B) and corresponding normal tissue (A) employing a primary antibody directed against tktl1. In the carcinoma of patient 1666 a strong overexpression of the tktl1 protein is detectable.

FIG. 9: Immunohistochemical analysis of gastric carcinoma patient 1682 (A) and 1697 (B) employing a primary antibody directed against tktl1. In the carcinoma of patient 1682 a strong overexpression of the tktl1 protein is detectable in the nucleus and the cytoplasm. In the carcinoma of patient 1697 a very strong overexpression of the tktl1 protein is detectable in the nucleus and the cytoplasm.

FIG. 10: Immunohistochemical analysis of gastric carcinoma patient 1699 employing a primary antibody directed against tktl1. FIG. A shows a carcinoma with an area of normal tissue. Whereas in the normal tissue a low expression of tktl1 is detectable a strong overexpression of tktl1 is present in the tumor cells of the carcinoma. A magnification of the border between normal and tumor tissue is shown in B. A tumor specific granular staining pattern is detectable.

FIG. 11: Immunohistochemical analysis of gastric carcinoma patient 1698 employing a primary antibody directed against tktl1. In FIG. A a strong overexpression of the tktl1 protein is detectable in the nucleus and the cytoplasm of gastric tumor cells. A low or absent expression is detectable in surrounding fibroblasts. A magnification of an area of carcinoma cells with surrounding connective tissue is shown in B. A tumor specific granular staining pattern is detectable.

Figure 1:
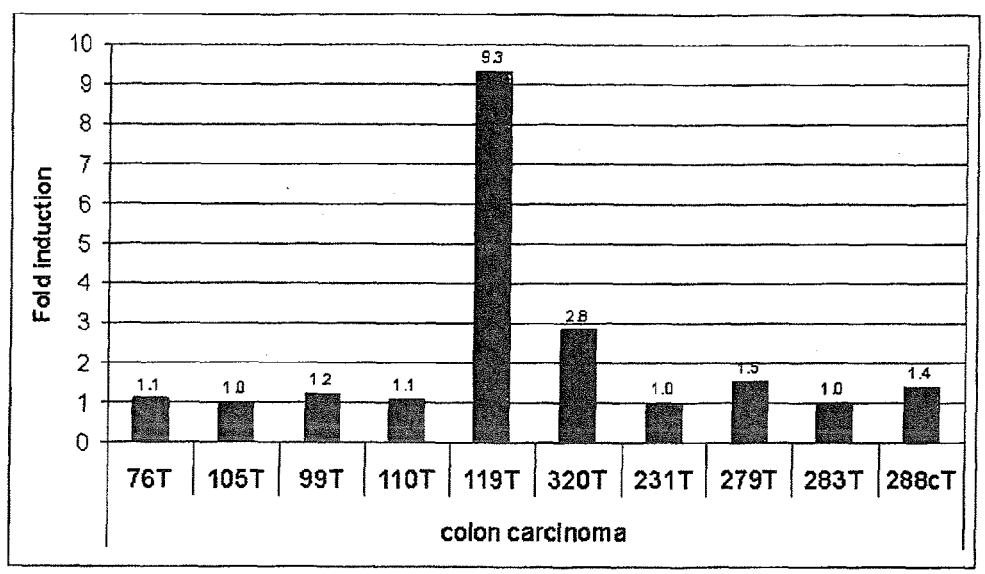
FIG. 1: Detection of the overexpression of transketolase like-1 gene by RT-PCR in colon carcinomas; the diagram shows the induction of expression of the transketolase like-1 gene in tissue of colon carcinoma in comparison to control tissue.
Figure 2:
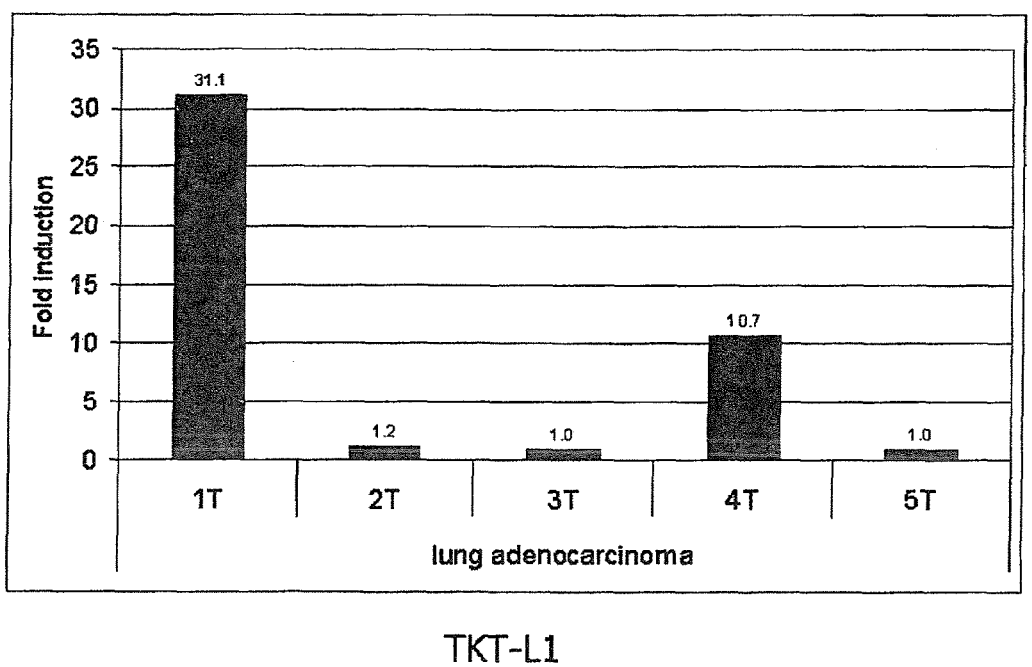
FIG. 2: Detection of the overexpression of transketolase like-1 gene by RT-PCR in lung adenocarcinomas; the diagram shows the induction of expression of the transketolase like-1 gene in tissue of lung adenocarcinoma in comparison to control tissue.
Figure 3:
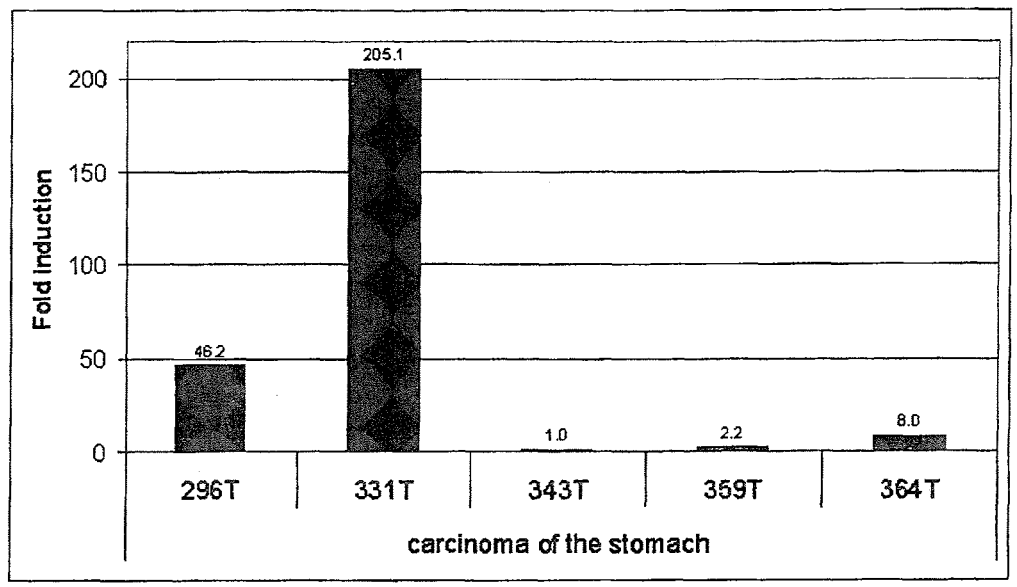
FIG. 3: Detection of the overexpression of transketolase like-1 gene by RT-PCR in carcinomas of the stomach; the diagram shows the induction of expression of the transketolase like-1 gene in tissue of carcinomas of the stomach in comparison to control tissue.
Figure 4:
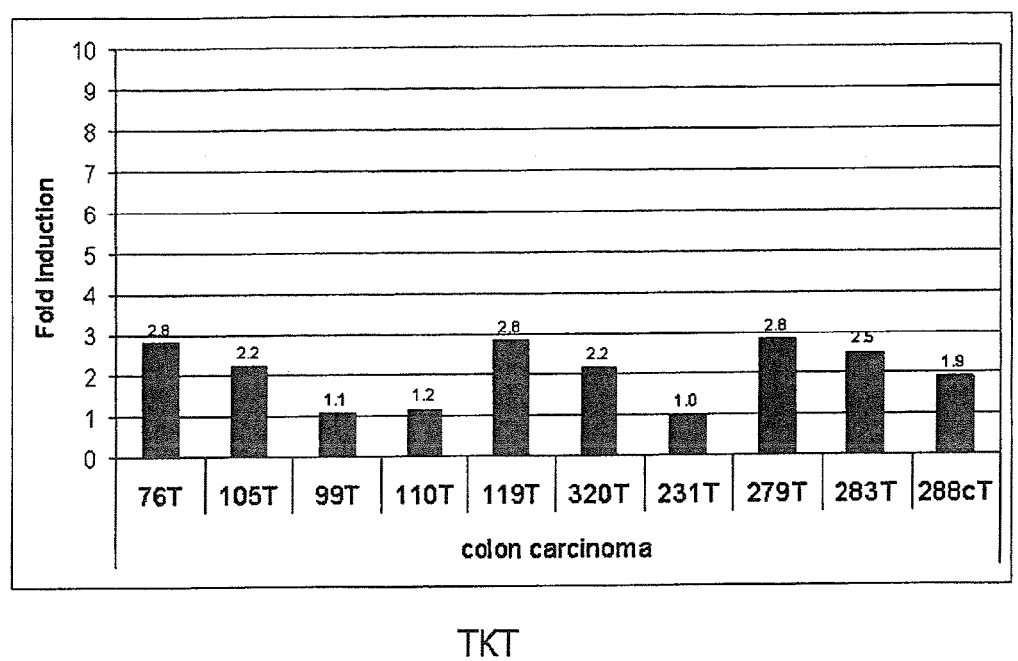
FIG. 4: Detection of the overexpression of transketolase by RT-PCR in colon carcinomas; the diagram shows the induction of expression of transketolase in tissue of colon carcinoma in comparison to control tissue.
Figure 5:
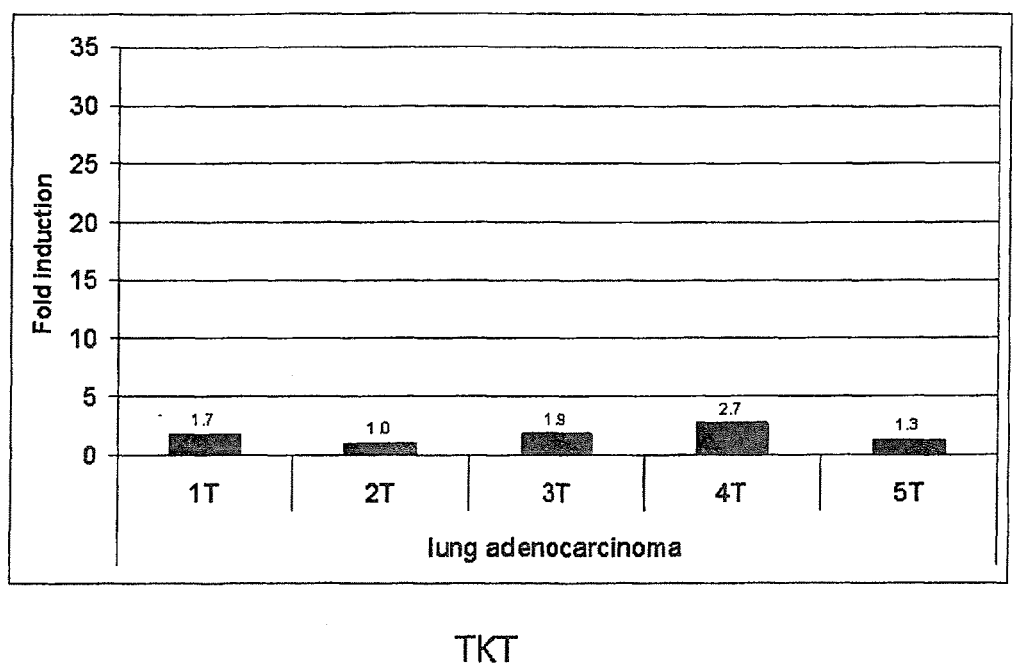
FIG. 5: Detection of the overexpression of transketolase by RT-PCR in lung adenocarcinomas; the diagram shows the induction of expression of transketolase in tissue of lung adenocarcinoma in comparison to control tissue.
Figure 6:
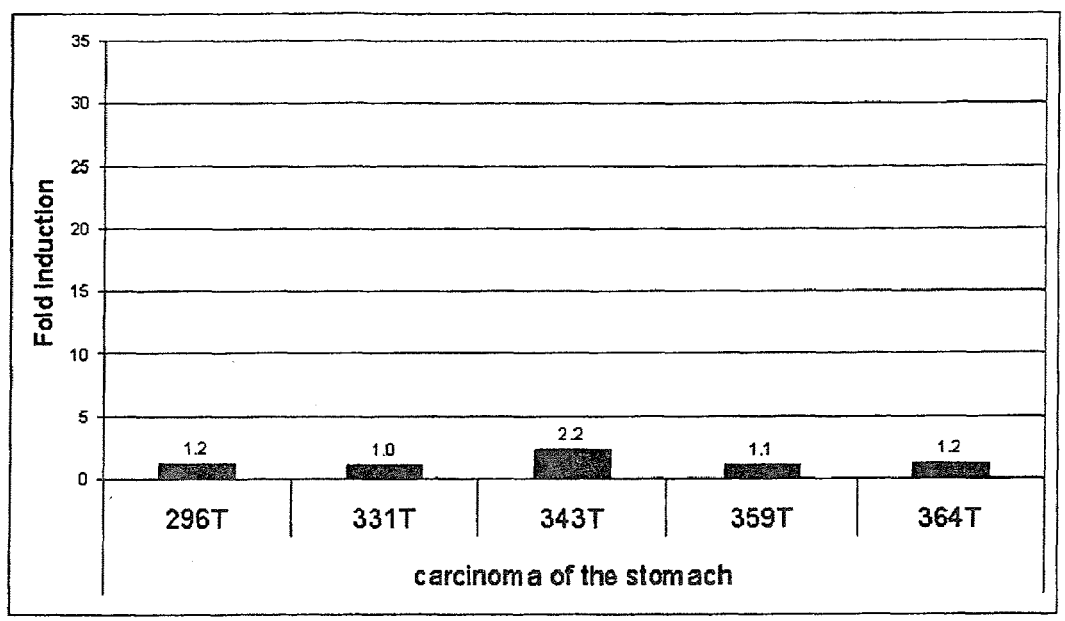
FIG. 6: Detection of the overexpression of transketolase by RT-PCR in carcinomas of the stomach; the diagram shows the induction of expression of transketolase in tissue of carcinoma of the stomach in comparison to control tissue.

The present invention provides methods for detection and treatment of disorders characterized by abnormal cell proliferation, such as e.g. cancers.

It is a first aspect of the present invention to provide a method for the detection of disorders characterized by abnormal cell proliferation, such as e.g. cancers based on the determination of the presence or absence and/or the level of expression of human transketolase like-1 gene as given in SEQ. ID. 1 (cf. TKT-L1, TKR: NM_012253; Accession number: X91817) in biological samples.

It is a second aspect of the present invention to provide a method for treatment of disorders characterized by abnormal cell proliferation, such as e.g. cancers using human transketolase like-1 gene products as therapeutically active agents.

A third aspect of the present invention is a research or diagnostic test kit for performing the reactions involved in the detection of the presence or absence and/or the level of overexpression of human transketolase like-1 gene.

A fourth aspect of the present invention relates to pharmaceutical compositions applicable in the treatment of disorders according to the present invention.

Transketolase like-1 gene products as used in the context of the present invention may comprise polypeptides and nucleic acids encoded by the transketolase like-1 gene.

The polypeptides and polynucleotides used for performing the method according to the present invention are isolated. This means that the molecules are removed from their original environment. Naturally occurring proteins are isolated if they are separated from some or all of the materials, which coexist in the natural environment. Polynucleotides are isolated for example if they are cloned into vectors.

Human transketolase like-1 nucleic acid molecules used for performing a method according to the present invention may comprise polynucleotides or fragments thereof. Preferred polynucleotides may comprise at least 20 consecutive nucleotides, preferably at least 30 consecutive nucleotides and more preferably at least 45 consecutive nucleotides, that are identical, share sequence homology or encode for identical, or homologous polypeptides, compared to the wild type transketolase like-1 polypeptides, but do not encode other transketolase like polypeptides or transketolases. The nucleic acids according to the present invention may also be complementary or reverse complementary to any of said polynucleotides. Polynucleotides may for example include single-stranded (sense or antisense) or double-stranded molecules, and may be DNA (genomic, cDNA or synthetic) or RNA. RNA molecules comprise as well hnRNA (containing introns) as mRNA (not containing introns). According to the present invention the polynucleotides may also be linked to any other molecules, such as support materials or detection marker molecules, and may, but need not, contain additional coding or non-coding sequences.

The human transketolase like-1 polynucleotides used according to the present invention may be native sequences or variants thereof. The variants may contain one or more substitutions, additions, deletions and/or insertions such that the immunogenicity of the encoded polypeptide is not diminished, relative to the native tumor protein. Variants may for example be allelic variations of the polynucleotides. Allelic variation as used herein is an alternative form of the gene, which may result from at least one mutation in the nucleic acid sequence. Alleles may result in altered mRNAs or polypeptides whose structure or function may or may not be altered. Any given gene may have none, one, or many allelic forms. Common mutational changes, which give rise to alleles, are generally ascribed to natural deletions, additions, or substitutions of nucleotides. Each of these types of changes may occur alone or in combination with the others, one or more times in a given sequence. The variants according to the present invention show preferably 70%, more preferably at least 80% and most preferably at least 90% of sequence identity to the native nucleic acid molecules disclosed herein. Methods for determination of sequence similarity are known to those of ordinary skill in the art.

One example for detecting the similarity of sequences may be carried out using the FastA and/or BlastN bioinformatics software accessible on the HUSAR server of the DKFZ Heidelberg.

Nucleic acids as used in the context of the present invention may be all polynucleotides, which hybridise to probes specific for the transketolase like-1 sequences used herein under stringent conditions. Stringent conditions applied for the hybridisation reaction are known to those of ordinary skill in the art and may be applied as described in Sambrook et al. Molecular cloning: A Laboratory Manual, 2nd Edition, 1989.

The present invention also comprises polynucleotides, that due to the degeneracy of the genetic code encode the polypeptides natively encoded by human transketolase like-1 nucleic acids while not showing the percentage of sequence homology as described above within the nucleic acid sequence. Such nucleic acids may for example arise by changing the codons present in the disclosed sequences by degenerate codons and so preparing a synthetic nucleic acid. The preparation of such artificial nucleic acid sequences may be achieved by the methods known to those skilled in the art.

The human transketolase like-1 nucleotide sequences used according to the present invention may be joined to a variety of other nucleic acid sequences using the known recombinant DNA techniques. The sequences may for example be cloned into any of a variety of cloning vectors, such as plasmid, phagemids, lambda phage derivatives and cosmids. Furthermore vectors such as expression vectors, replication vectors, probe generation vectors and sequencing vectors may be joined with the sequences disclosed herein.

Sequences that may be cloned to the nucleic acids according to the present invention comprise as well coding sequences as non-coding sequences and regulatory sequences including promoters, enhancers and terminators. The human transketolase like-1 nucleic acid sequences disclosed herein might for example be present in combination with other coding sequences. These sequences may encode for a variety of proteins such as enzymes, receptors, antigens, immunogenic fragments or epitopes, binding proteins, etc. The nucleic acid sequences may be joined directly or may be separated by a stretch of nucleic acids coding for a spacer or linker region. The nucleic acid sequences may also be separated by a stretch of nucleic acids that may be removed after transcription of the sequence. Non-coding sequences, that may be joined to the sequences disclosed herein may for example be promoter regions, enhancers, cis regulatory elements, 5' untranslated regions, terminators etc.

In a preferred embodiment human transketolase like-1 polynucleotides may be formulated such, that they are able to enter prokaryotic or eukaryotic cells such as mammalian cells and to be expressed in said cells. Such formulations may be for example useful for therapeutic purposes. The expression of nucleic acid sequences in target cells may be achieved by any method known to those skilled in the art. The nucleic acids may for example be joined to elements that are apt to enable their expression in a host cell. Such elements may comprise promoters or enhancers, such as CMV-, SV40-, RSV-, metallothionein I- or polyhedrin-promoters respectively CMV- or SV40-enhancers. Possible methods for the expression are for example incorporation of the polynucleotide into a viral vector including adenovirus, adeno-associated virus, retrovirus, vaccinia virus or pox virus. Viral vectors for the purpose of expression of nucleic acids in mammalian host cells may comprise pcDNA3, pMSX, pKCR, pEFBOS, cDMB, pCEV4 etc. These techniques are known to those skilled in the art.

Fragments of the human transketolase like-1 sequence used herein may comprise oligonucleotides such as nucleic acid probes for hybridisation purposes, primers for amplification reactions or antisense constructs for use in antisense techniques. Nucleic acid probes according to the present invention may be any nucleic acid probe that has a sequence at least 80% identical to a part of at least 15 consecutive nucleotides of the human transketolase like-1 gene nucleic acid sequence or is complementary or reverse complementary to such a sequence but does not hybridise to an other transketolase or transketolase like sequence. The nucleic acid probes according to the present invention are furthermore characterized, in that they hybridise under stringent conditions to nucleic acids of the sequence disclosed herein. Primers may be any nucleotides that are suitable for carrying out a specific amplification reaction. Thus the primers used according to the present invention may be nucleic acid oligomers of at least 15 consecutive nucleotides with a sequence identity of at least 80% compared to the human transketolase like-1 gene sequence or may be complementary or reverse complementary to such a sequence. The primers according to the present invention specifically hybridise to the sequence disclosed herein or a part thereof under conditions suitably applied in the course of a nucleic acid amplification reaction but do not hybridise to an other transketolase or transketolase like sequence. Antisense oligonucleotides as used herein may be nucleic acid molecules reverse complementary to the transcripts of the disclosed coding sequence, that are able to bind to the transcripts by base pairing and such inhibit or reduce expression of said coding sequence.

The nucleic acids used according to the present invention may also be chemically pre-treated nucleic aids. Such chemically pre-treated nucleic acids may comprise any nucleic acid as disclosed herein, which has been treated with a chemical agent suitable to result in modifications in the nucleic acid molecules. Said modifications may for example comprise specific modifications of particular bases within the nucleic acid. Such chemical treatments may comprise treatment with e.g. sodium bisulphite, hydrazine or potassium permanganate. The sequences of special interest in experiments using chemical pre-treatment of nucleic acids may for example comprise coding or non-coding regions of the sequences. Examples of non-coding regions that may be treated by chemicals are promoter regions or CpG islands in 5' UTRs.

Human transketolase like-1 polypeptides as used according to the present invention may comprise amino acid chains of any length, including full length proteins, wherein the amino acid residues are linked by covalent peptide bonds. Thus, a polypeptide comprising a portion of one of the above human transketolase like-1 proteins, e.g. a protein comprising the amino acid sequence of human transketolase like-1 protein, may consist entirely of the portion, or the portion may be present within a larger polypeptide that contains additional sequences. The additional sequences may be derived from the native protein or may be heterologous, and such sequences may (but need not) be immunoreactive and/or antigenic. As detailed below, such polypeptides may be isolated from tumor tissue or prepared by synthetic or recombinant means.

As used herein, a polypeptide exhibiting biological properties of the human transketolase like-1 polypeptide is understood to be a polypeptide having at least one of the activities, such as enzymatic activities (transketolase activity), inter protein interaction activities, responsiveness of the enzymatic activity to thiamine presence, or antigenic or immunogenic properties e.g. capability of binding an antibody directed against said polypeptide (i.e. comprising an immunogenic portion) of said human transketolase like-1 polypeptide.

Immunogenic portion as used herein is a portion of a protein that is recognized by a B-cell and/or T-cell surface antigen receptor. The immunogenic portions comprise at least 5 amino acid residues, more preferably at least 10 amino acid residues and most preferably at least 15 amino acid residues of the protein disclosed herein. In a preferred embodiment of the present invention, particular domains of the protein, such as for example transmembrane domains or N-terminal leader sequences have been deleted.

The immunogenic portions according to the present invention react with antisera or specific antibodies in the same or nearly same intensity as the native full length proteins. The immunogenic portions are generally identified using the techniques well known in the art. Possible techniques are for example screening of the polypeptides for the ability to react with antigen-specific antibodies, antisera and/or T-cell lines or clones.

The human transketolase like-1 polypeptides used according to the present invention comprise also variants of the native proteins. These variants may differ from the native protein in one or more alterations such as substitutions, deletions, additions and/or insertions. The immunoreactivity and or biological activity of the variants according to the present invention is not substantially diminished compared to the native proteins. In a preferred embodiment of the invention the immunoreactivity and or activity is diminished less than 50%, in a more preferred embodiment the immunoreactivity and or activity is diminished less than 20% compared to the native polypeptides. In another preferred embodiment of the present invention the variants of the polypeptides may be varied, such that the activity of the native protein is increased, decreased or lost. These variants may for example be employed in the therapy of disorders associated with the overexpression of human transketolase like-1 gene. In a preferred embodiment variants may be deficient in one or more portions, such as for example N-terminal leader sequences, transmembrane domains or small N- and/or C-terminal sequences. The variants exhibit preferably 70%, more preferably at least 90% and most preferably at least 95% identity to the polypeptides disclosed according to the present invention.

The variants used according to the present invention comprise preferably conservative substitutions, so that the amino acids changed are substituted for amino acids with similar properties. The properties concerned may include polarity, charge, solubility, hydrophobicity, hydrophilicity and/or amphipathic nature of the amino acid residues.

The variants used according to the invention may also comprise additional terminal leader sequences, linkers or sequences, which enable synthesis, purification or stability of the polypeptides in an easier or more comfortable way.

Variants of the polypeptides used in the methods according to the present invention may be produced by means of conventional molecular biological processes (see, e.g., Sambrook et al., 1989, Molecular Cloning, A Laboratory Manual, 2nd edition Cold Spring Harbor Laboratory Press, Cold Spring Harbor, N.Y.) For example it is possible to introduce different mutations into the nucleic acid molecules of the invention. As a result a human transketolase like-1 polypeptide with possibly modified biological properties may be synthesized. One possibility is the production of deletion mutants in which nucleic acid molecules are produced by continuous deletions from the 5'- or 3'-terminal of the coding DNA sequence and that lead to the synthesis of polypeptides that are shortened accordingly. Another possibility is the introduction of single-point mutations at positions where a modification of the amino acid sequence influences, e.g., the enzyme activity or the regulation of the enzyme. By this method muteins can be produced, for example, that possess a modified Km-value or that are no longer subject to the regulation mechanisms that normally exist in the cell, e.g. with regard to allosteric regulation or covalent modification. Such muteins might e.g. be valuable as therapeutically useful compounds, e.g. antagonists.

For the manipulation in prokaryotic cells by means of genetic engineering the nucleic acid molecules used for the methods of the invention or parts of these molecules can be introduced into plasmids allowing a mutagenesis or a modification of a sequence by recombination of DNA sequences. By means of conventional methods (cf. Sambrook et al., supra) bases may be exchanged and natural or synthetic sequences may be added. In order to link the DNA fragments with each other, adapters or linkers may be added to the fragments. Furthermore, manipulations may be performed that provide suitable cleavage sites or that remove superfluous DNA or cleavage sites. If insertions, deletions or substitutions are possible, in vitro mutagenesis, primer repair, restriction or ligation may be performed. As analysis method usually sequence analysis, restriction analysis and other biochemical or molecular biological methods may be used.

The polypeptides may comprise fusion or chimeric polypeptides containing sequences disclosed herein. Fusion proteins comprise the inventive polypeptide, a portion thereof or variants of the inventive polypeptide or portions thereof together with any second and further polypeptides, such as once more the inventive polypeptide, a portion thereof or variants of the inventive polypeptide or portions thereof and/or any heterologous polypeptides. Heterologous polypeptides may comprise enzymes, receptor molecules, antigens, antigenic or immunogenic epitopes or fragments thereof, antibodies or fragments thereof, signalling polypeptides or signal transducing polypeptides etc. The immunogenic protein may for example be capable of eliciting a recall response. Examples of such proteins include tetanus, tuberculosis and hepatitis proteins (see, for example, Stoute et al. New Engl. J. Med., 336:86-91 (1997)). In one embodiment of the invention the fusion peptides may be constructed for enhanced detection or purification of the polypeptides. For the purpose of purification tags, such as e.g. his-tags, myc-tags etc. may be added to the polypeptides. For the purpose of detection antigenic portions, enzymes, chromogenic sequences etc. may be fused to the polypeptides. The fusion proteins of the present invention may (but need not) include a linker peptide between the first and second polypeptides.

A nucleic acid sequence encoding a fusion protein used in the present invention is constructed using known recombinant DNA techniques to assemble separate nucleic acid sequences encoding the first and second polypeptides into an appropriate expression vector. The 3' end of a nucleic acid sequence encoding the first polypeptide is ligated, with or without a peptide linker, to the 5' end of a nucleic acid sequence encoding the second polypeptide ensuring the appropriate reading frames of the sequences to permit mRNA translation of the two nucleic acid sequences into a single fusion protein that retains the biological activity of both the first and the second polypeptides.

A peptide linker sequence may be employed to separate the first and the second polypeptides by a distance sufficient to ensure, that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may be from 1 to about 50 amino acids in length. Peptide sequences are not required when the first and second polypeptides have non-essential N-terminal amino acid regions that can be used to separate the functional domains and prevent steric interference.

The human transketolase like-1 polypeptides for use in the method according to the present invention and nucleic acids encoding such polypeptides, may be isolated from tumor tissue using any of a variety of methods well known in the art. Nucleic acid sequences corresponding to a gene (or a portion thereof) encoding one of the inventive tumor polypeptides may be isolated from a tumor cDNA library using a subtraction technique. Partial nucleic acid sequences thus obtained may be used to design oligonucleotide primers for the amplification of full-length nucleic acid sequences from a human genomic nucleic acid library or from a tumor cDNA library in a polymerase chain reaction (PCR), using techniques well known in the art (see, for example, Mullis et al., Cold Spring Harbor Symp. Quant. Biol. 51:263, 1987; Erlich ed., PCR Technology, Stockton Press, New York, 1989). For this approach, sequence-specific primers may be designed based on the nucleotide sequences provided herein and may be purchased or synthesized.

The human transketolase like-1 polypeptides used for the method disclosed herein may also be generated by synthetic means. In particular, synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (see, for example, Merrifield, J. Am. Chem. Soc. 85:2149-2146, 1963). Equipment for automated synthesis of polypeptides is commercially available from suppliers such as Perkin Elmer/Applied BioSystems Division (Foster City, Calif.), and may be operated according to the manufacturer's instructions.

The ligated nucleic acid sequences encoding the polypeptides used for the methods disclosed herein are operably linked to suitable transcriptional or translational regulatory elements known to the person skilled in the art. The regulatory elements responsible for expression of nucleic acid may be located e.g. 5' to the nucleic acid sequence encoding the first polypeptides, within the coding sequences or 3' to the nucleic acid sequences encoding the first or any further polypeptide. Stop codons required to end translation and transcription termination signals are present 3' to the nucleic acid sequence encoding the second polypeptide.

The polypeptides used for the methods according to the present invention may be isolated. This means that the molecules may be removed from their original environment. Naturally occurring proteins are isolated if they are separated from some or all of the materials, which coexist in the natural environment. Polynucleotides are isolated for example if they are cloned into vectors.

In certain preferred embodiments, described in more detail below, the polypeptides used in a method as disclosed herein may be prepared in an isolated, substantially pure form (i.e., the polypeptides are homogenous as determined by amino acid composition and primary sequence analysis). Preferably, the polypeptides are at least about 90% pure, more preferably at least about 95% pure and most preferably at least about 99% pure. The substantially pure polypeptides may for example be employed in pharmaceutical compositions.

Furthermore the present invention makes use of binding agents that specifically bind to a human transketolase like-1 protein. These binding agents may comprise for example antibodies and antigen-binding fragments, bifunctional hybrid antibodies, peptidomimetics containing minimal antigen-binding epitopes etc.

An antibody or antigen-binding agent is said to react specifically, if it reacts at a detectable level with a protein used herein, and does not significantly react with other proteins. The antibodies according to the present invention may be monoclonal or polyclonal antibodies. As used herein, the term antibody or monoclonal antibody is meant to include intact molecules as well as antibody fragments (such as, for example, Fab and F(ab')2 fragments), which are capable of specifically binding to protein. Fab and F(ab')2 fragments lack the Fc fragment of intact antibody, clear more rapidly from the circulation, and may have less non-specific tissue binding than an intact antibody (Wahl et al., J. Nucl. Med. 24:316-325 (1983). Thus, these fragments are preferred, as well as the products of a Fab or other immunoglobulin expression library. Moreover, antibodies used in the present invention include chimeric, single chain, and humanized antibodies.

According to the present invention binding agents may be used isolated or in combination. By means of combination it is possible to achieve a higher degree of sensitivity. The term antibody, preferably, relates to antibodies, which consist essentially of pooled monoclonal antibodies with different epitopic specificities, as well as distinct monoclonal antibody preparations.

Monoclonal antibodies are made from an antigen containing fragments of the polypeptide used in the invention using any of a variety of techniques known to those of ordinary skill in the art; see, e.g., Harlow and Lane, Antibodies: A Laboratory Manual, Cold Spring Harbor Laboratory, 1988. In one such technique, an immunogen comprising the antigenic polypeptide or a synthetic part thereof is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic polypeptide of interest may be prepared, for example, using the technique of Köhler and Milstein, Eur. J. Immunol. 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a non-ionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The human transketolase like-1 polypeptides may be used in the purification process in, for example, an affinity chromatography step.

The human transketolase like-1 specific antibodies used according to the present invention may comprise further binding sites for either therapeutic agents or other polypeptides or may be coupled to said therapeutic agents or polypeptides. Therapeutic agents may comprise drugs, toxins, radio nuclides and derivatives thereof. The agents may be coupled to the binding agents either directly or indirectly for example by a linker or carrier group. The linker group may for example function in order to enable the coupling reaction between binding agent and therapeutic or other agent or the linker may act as a spacer between the distinct parts of the fusion molecule. The linker may also be cleavable under certain circumstances, so as to release the bound agent under said conditions. The therapeutic agents may be covalently coupled to carrier groups directly or via a linker group. The agent may also be non-covalently coupled to the carrier. Carriers that can be used according to the present invention are for example albumins, polypeptides, polysaccharides or liposomes.

The human transketolase like-1 specific antibodies used according to the present invention may be coupled to one or more agents. The multiple agents coupled to one antibody may be all of the same species or may be several different agents bound to one antibody.

The methods disclosed herein are applicable to all eukaryotic organisms prone to be affected by disorders associated with the overexpression of transketolase like-1 gene. Individuals as used in the context of the present invention may for example comprise mammals, such as animals of agricultural interest (cows, sheep, horses, pigs, etc.), companion animals (cats, dogs, etc.), animals commonly employed for research use (rats, mice, hamsters, etc.) or human beings.

Diagnosis as used in the context of the present invention may comprise determining the level of human transketolase like-1 gene products in a sample. Based upon the determined level of human transketolase like-1 gene products in the samples individuals can be subdivided into subgroups. The subgroups may be created according to clinical data, such as e.g. survival, recurrence of disease, frequency of metastases etc., related to the particular level of transketolase like-1 gene products determined in the samples.

Based upon these subgroups an assessment of prognosis may be done. According to the subgroups the therapy of the individuals affected by the tumors may be tailored.

For example the overexpression of transketolase like-1 gene and an enhanced activity of the pentose-phosphate cycle in a subset of colon, stomach, pancreas and lung tumors suggest a mechanism by which thiamine (vitamin B1) promotes nucleic acid ribose synthesis and tumor cell proliferation via the nonoxidative transketolase pathway. Therefore the thiamine intake of cancer patients has direct consequences for the growth rate of tumors with an overexpression of the transketolase like-1 gene. This provides also background information and helps to develop guidelines for alternative treatments with antithiamine transketolase inhibitors in the clinical setting. Clinical and experimental data demonstrate increased thiamine utilization of human tumors and its interference with experimental chemotherapy. Analysis of RNA ribose indicates that glucose carbons contribute to over 90% of ribose synthesis in cultured cervix and pancreatic carcinoma cells and that ribose is synthesized primarily through the thiamine dependent transketolase pathway (>70%). Antithiamine compounds significantly inhibit nucleic acid synthesis and tumor cell proliferation in vitro and in vivo in several tumor models. The medical literature reveals little information regarding the role of the thiamine dependent transketolase reaction in tumor cell ribose production, which is a central process in de novo nucleic acid synthesis and the salvage pathways for purines.

As thiamine dependent transketolase pathway is the central avenue supplying ribose phosphate for nucleic acids in tumors an excessive thiamine supplementation may be responsible for failed therapeutic attempts to terminate cancer cell proliferation. The detection of a subset of colon and lung tumors with an overexpression of the transketolase like-1 gene provides an important step to an individualized cancer therapy and limited administration of thiamine and concomitant treatment with transketolase inhibitors is a more rational approach to treat cancer.

Thus based on the detection of overexpression of TKT-L1 new treatment strategies may be tailored targeting specific biochemical reactions of pentose-phosphate cycle by hormones related to glucose metabolism, controlling thiamine intake, the cofactor of the nonoxidative transketolase pentose-phosphate cycle reaction, or treating cancer patients with antithiamine analogues.

Thus in one embodiment of the invention disorders characterized by overexpression of human transketolase like-1 gene may be treated in accordance to the level of overexpression of transketolase like-1 gene. Using the non-oxidative pentose-phosphate cycle reactions to inhibit glucose utilizing pathways selectively for nucleic acid production offers a new target site for cancer treatment with a strong regulatory effect on the cell cycle.

In one embodiment the treatment of disorders associated with overexpression of transketolase like-1 gene may comprise restricted administration of thiamine to the affected individuals. In another embodiment the treatment may comprise the administration of transketolase inhibitors, such as e.g. antithiamine compounds.

Monitoring may comprise detecting the level of human transketolase like-1 gene products in samples taken at different points in time and determining the changes in said level. According to said changes the course of the disease can be followed. The course of the disease may be used to select therapy strategies for the particular individual.

Another aspect of diagnosis and monitoring of the disease course according to the present invention may comprise the detection of minimal residual disease. This may comprise for example the detection of a human transketolase like-1 gene products level in one or more body samples following initial therapy of an individual once or at several time points.

According to the level of human transketolase like-1 gene products detected in the samples one may select a suitable therapy for the particular individual.

In another preferred embodiment the diagnostic method is carried out to detect disseminated tumor cells in biological samples as diagnosis of minimal residual disease (MRD).

Disorders characterized by abnormal cell proliferation, as used in the context of the present invention, may comprise for example neoplasms such as benign and malignant tumors, carcinomas, sarcomas, leukemias, lymhomas or dysplasias. Tumors may comprise tumors of the head and the neck, tumors of the respiratory tract, tumors of the gastrointestinal tract, tumors of the urinary system, tumors of the reproductive system, tumors of the endocrine system, tumors of the central and peripheral nervous system, tumors of the skin and its appendages, tumors of the soft tissues and bones, tumors of the lymphopoietic and hematopoietic system etc.

In a preferred embodiment the tumor is for example cancer of the of the head and the neck, cancer of the respiratory tract, cancer of the gastrointestinal tract, cancer of the skin and its appendages, cancer of the central and peripheral nervous system, cancer of the urinary system, cancer of the reproductive system, cancer of the endocrine system, cancer of the soft tissues and bone, cancer of the hematopoietic and lymphopoietic system. In the most preferred embodiment of the invention the carcinoma is cervical cancer, colon cancer, gastric cancer, breast cancer, bladder cancer etc.

The tumors according to the present invention may comprise tumors, which show detectable lymph-node involvement (node positive tumors) as well as tumors, without detectable spread to lymph-nodes (node negative tumors). In one embodiment of the invention the gastrointestinal tumors are tumors without detectable spread to lymph nodes.

A sample according to the method of the present invention may comprise any sample comprising cells or cell debris. Samples may comprise samples of clinical relevance, such as e.g. secretions, such as gastric juice, bile or pancreatic juice, smears, body fluids, such as serum, blood, plasma urine, semen, stool, biopsies or cell- and tissue-samples. Biopsies as used in the context of the present invention may comprise e.g. resection samples of tumors, tissue samples prepared by endoscopic means or needle biopsies of organs. Furthermore any sample potentially containing the marker molecules to be detected may be a sample according to the present invention.

Such samples may comprise for example intact cells, lysed cells or any liquids containing proteins, peptides or nucleic acids. Even solids, to which cells, cell fragments or marker molecules, such as human transketolase like-1 nucleic acids or human transketolase like-1 proteins, may adhere may be samples according to the present invention. Such solids may comprise for example membranes, glass slides, beads etc.

Preparation of a sample may comprise e.g. obtaining a sample of a tissue, a body fluid, of cells, of cell debris from a patient. According to the present invention preparation of the sample may also comprise several steps of further preparations of the sample, such as preparation of dissections, preparation of lysed cells, preparation of tissue arrays, isolation of polypeptides or nucleic acids, preparation of solid phase fixed peptides or nucleic acids or preparation of beads, membranes or slides to which the molecules to be determined are coupled covalently or non-covalently.

The method for detection of the level of the human transketolase like-1 gene product according to the present invention is any method, which is suited to detect very small amounts of specific biologically active molecules in biological samples. The detection reaction according to the present invention is a detection either on the level of nucleic acids or on the level of polypeptides.

The detection may be carried out in solution or using reagents fixed to a solid phase. The detection of one or more molecular markers, such as polypeptides or nucleic acids, may be performed in a single reaction mixture or in two or separate reaction mixture. Alternatively the detention reactions for several marker molecules may for example be performed simultaneously in multi-well reaction vessels. The markers characteristic for the human transketolase like-1 gene products may be detected using reagents that specifically recognise these molecules. The detection reaction for the marker molecules may comprise one or more reactions with detecting agents either recognizing the initial marker molecules or recognizing the prior molecules used to recognize other molecules.

The detection reaction further may comprise a reporter reaction indicating the presence or absence and/or the level of the human transketolase like-1 gene markers. The reporter reaction may be for example a reaction producing a coloured compound, a bioluminescence reaction, a fluorescence reaction, generally a radiation emitting reaction etc. In a preferred embodiment, different marker molecules may be recognized by agents that produce different reporter signals, so that the signals referring to marker molecules could be distinguished.

Applicable formats for the detection reaction according to the present invention may be, blotting techniques, such as Western-Blot, Southern-blot, Northern-blot. The blotting techniques are known to those of ordinary skill in the art and may be performed for example as electro-blots, semidry-blots, vacuum-blots or dot-blots. Amplification reaction may also be applicable for the detection of e.g. nucleic acid molecules. Furthermore immunological methods for detection of molecules may be applied, such as for example immunoprecipitation or immunological assays, such as ELISA, RIA, lateral flow assays, immuno-cytochemical methods etc.

In one preferred embodiment of the invention the detection of the level of human transketolase like-1 gene products is carried out by detection of the level of nucleic acids coding for the human transketolase like-1 gene products or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognizing and binding to said nucleic acids. This method can be performed as well in vitro as directly in situ for example in the course of a detecting staining reaction. Another way of detecting the human transketolase like-1 gene products in a sample on the level of nucleic acids performed in the method according to the present invention is an amplification reaction of nucleic acids, which can be carried out in a quantitative manner such as for example the polymerase chain reaction. In a preferred embodiment of the present invention real time RT PCR may be used to quantify the level of transketolase like-1 RNA in samples of tumors.

In another preferred embodiment of the invention the detection of the level of human transketolase like-1 gene products is carried out by determining the level of expression of a protein. The determination of the human transketolase like-1 gene products on the protein level can for example be carried out in a reaction comprising an antibody specific for the detection of the human transketolase like-1 protein. The antibodies can be used in many different detection techniques for example in Western-blot, ELISA or immunoprecipitation.

Generally antibody based detection can be carried out as well in vitro as directly in situ for example in the course of an immuno-histochemical staining reaction. Any other method for determining the amount of particular polypeptides in biological samples can be used according to the present invention.

In one preferred embodiment of the invention the level of human transketolase like-1 gene products is significantly elevated compared to a control test sample. In this case the human transketolase like-1 gene is overexpressed in the sample.

One example for the diagnosis of disorders associated with the expression of the human transketolase like-1 gene may comprise the detection of auto-antibodies directed against polypeptides encoded by the human transketolase like-1 gene. The polypeptides used for the methods according to the present invention may be used to detect the presence or absence of such antibodies in body fluids by methods known to those of skill in the art.

In one preferred embodiment the detection of tissues expressing transketolase like-1 gene products is carried out in form of molecular imaging procedures. The respective procedures are known to those of ordinary skill in the art. Imaging methods for use in the context of the present invention may for example comprise MRI, SPECT, PET and other methods suitable for in vivo imaging.

In one embodiment the method may be based on the enzymatic conversion of inert or labelled compounds to molecules detectable in the course of molecular imaging methods by the transketolase like-1 molecules. In another embodiment the molecular imaging method may be based on the use of compounds carrying a suitable label for in vivo molecular imaging, such as radio isotopes, metal ions etc., specifically binding to transketolase like-1 molecules in vivo.

In a preferred embodiment of the invention these compounds are non-toxic compounds and may be eliminated from the circulation of organisms, such as humans, in a time span, that allows for performing the detection of label accumulated in tumor tissue overexpressing transketolase like-1 gene. In another preferred embodiment of the invention compounds are used for molecular imaging, for which clearance from the circulation is not relevant for performing the molecular imaging reaction. This may be for example due to low background produced by the circulating molecules etc. The compounds for use in molecular imaging methods are administered in pharmaceutical acceptable form in compositions that may additionally comprise any other suitable substances, such as e.g. other diagnostically useful substances, therapeutically useful substances, carrier substances or the like.

Another aspect of the present invention is a testing kit for performing the method according to the present invention. The kit may be for example a diagnostic kit or a research kit.

A kit according to the present invention comprises at least an agent suitable for detecting the molecules disclosed herein. Furthermore a kit according to present invention may comprise:
a) reagents for the detection of the human transketolase like-1 gene products
b) reagents and buffers commonly used for carrying out the detection reaction, such as buffers, detection-markers, carrier substances and others
c) a human transketolase like-1 sample for carrying out a positive control reaction The reagent for the detection of the human transketolase like-1 gene may include any agent capable of binding to the human transketolase like-1 molecule. Such reagents may include proteins, polypeptides, nucleic acids, peptide nucleic acids, glycoproteins, proteoglycans, polysaccharides or lipids.

The human transketolase like-1 sample for carrying out a positive control may comprise for example human transketolase like-1 nucleic acids or polypeptides or fragments thereof in applicable form, such as solution or salt, peptides in applicable form, tissue section samples or positive cells.

In a preferred embodiment of the invention the detection of the human transketolase like-1 gene product is carried out on the level of polypeptides. In this embodiment the binding agent may be for example an antibody specific for the human transketolase like-1 or a fragment thereof.

In an other embodiment of the test kit the detection of the human transketolase like-1 gene products is carried out on the nucleic acid level. In this embodiment of the invention the reagent for the detection may be for example a nucleic acid probe or a primer reverse-complementary to said human transketolase like-1 nucleic acid.

In a further aspect the present invention relates to the use of one or more of the compounds useful for the methods according to the present invention such as a nucleic acid molecule, a recombinant vector, a polypeptide, an antisense RNA sequence, a ribozyme or an antibody for the preparation of a pharmaceutical composition for the treatment of cancer, preferably colon cancer, pancreatic carcinoma, gastric cancer, lung cancer.

The polypeptides, polynucleotides and binding agents useful in the method according to the present invention may be incorporated into pharmaceutical or immunogenic compositions. The pharmaceutical compositions comprise said compounds and a physiologically acceptable carrier.

A pharmaceutical composition or vaccine may for example contain DNA that codes for one or more polypeptides according to the present invention. The DNA may be administered in a way that allows the polypeptides to be generated in situ. Suitable expression systems are known to those skilled in the art. The expression of the polypeptides may for example be persistent or transient. In pharmaceutical compositions and/or vaccines, providing for in-situ expression of polypeptides, the nucleic acids may be present within any suitable delivery system known to those of ordinary skill in the art, including nucleic acid expression systems, bacteria and viral expression systems. Appropriate nucleic acid expression systems comprise the necessary regulatory nucleic acid sequences for expression in the patient, such as suitable promoters, terminators etc. Bacterial delivery systems may for example employ the administration of a bacterium that expresses an epitope of a cell antigen on its cell surface. In a preferred embodiment, the nucleic acid may be introduced using a viral expression system such as e.g., vaccinia virus, retrovirus, or adenovirus, which may involve the use of a non-pathogenic, replication competent virus. Suitable systems are disclosed, for example, in Fisher-Hoch et al., PNAS 86:317-321, 1989; Flexner et al., Ann. N.Y. Acad Sci. 569:86-103, 1989; Flexner et al., Vaccine 8:17-21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616-627, 1988; Rosenfeld et al., Science 252:431-434, 1991; Kolls et al., PNAS 91:215-219, 1994; Kass-Eisler et al., PNAS 90:11498-11502, 1993; Guzman et al., Circulation 88:2838-2848, 1993; and Guzman et al., Cir. Res. 73:1202-1207, 1993. In another embodiment transgenic mammalian cells may be used for delivery and/or expression of the nucleic acids. The methods for producing nucleic acid constructs suitable for in-situ expression of polypeptides are known to those of skill in the art.

In another embodiment of the invention the nucleic acids may be for example anti-sense constructs.

The nucleic acid may also be administered as a naked nucleic acid. In this case appropriate physical delivery systems, which enhance the uptake of nucleic acid may be employed, such as coating the nucleic acid onto biodegradable beads, which are efficiently transported into the cells. Administration of naked nucleic acids may for example be useful for the purpose of transient expression within a host or host cell.

Alternatively the pharmaceutical compositions may comprise one or more polypeptides. The polypeptides incorporated into pharmaceutical compositions may be the human transketolase like-1 polypeptides in combination with one or more other known polypeptides such as for example enzymes, antibodies, regulatory factors, such as cyclins, cyclin-dependent kinases or CKIs, or toxins.

The pharmaceutical compositions may be administered by any suitable way known to those of skill in the art. The administration may for example comprise injection, such as e.g., intracutaneous, intramuscular, intravenous or subcutaneous injection, intranasal administration for example by aspiration or oral administration. A suitable dosage to ensure the pharmaceutical benefit of the treatment should be chosen according the parameters, such as age, sex, body weight etc. of the patient, known to those of skill in the art.

The type of carrier to be employed in the pharmaceutical compositions of this invention, will vary depending on the mode of administration. For parenteral administration, such as subcutaneous injection, the carrier preferably comprises water, saline, alcohol, a lipid, a wax and/or a buffer. For oral administration, any of the above carriers or a solid carrier, such as mannitol, lactose, starch, magnesium stearate, sodium saccharine, talcum, cellulose, glucose, sucrose, and/or magnesium carbonate, may be employed. Biodegradable microspheres (e.g., polylactic glycolide) may also be employed as carriers for the pharmaceutical compositions of this invention. Suitable biodegradable microspheres are disclosed, for example, in U.S. Pat. Nos. 4,897,268 and 5,075,109.

The compounds of the present invention may furthermore be incorporated into immunogenic compositions.

The constituents of an immunogenic composition may comprise vaccines, antigens, antigenic fragments or nucleic acids coding for antigens or antigenic fragments to be expressed in situ. This compounds may be present polypeptides, or as nucleic acids, that allow the polypeptides to be expressed in situ. Immunogenic compositions comprise said compounds and additionally an immunostimulant or immunogenic adjuvant.

Polypeptides of the present invention or fragments thereof, that comprise an immunogenic portion of a human transketolase like-1 protein, may be used in immunogenic compositions, wherein the polypeptide e.g. stimulates the patient's own immune response to tumor cells. A patient may be afflicted with disease, or may be free of detectable disease. Accordingly, the compounds disclosed herein may be used to treat cancer or to inhibit the development of cancer. The compounds may be administered either prior to or following a conventional treatment of tumors such as surgical removal of primary tumors, treatment by administration of radiotherapy, conventional chemotherapeutic methods or any other mode of treatment of the respective cancer or its precursors.

Immunogenic compositions such as vaccines may comprise one or more polypeptides and a non-specific immune-response enhancer, wherein the non-specific immune response enhancer is capable of eliciting or enhancing an immune response to an exogenous antigen. Examples of non-specific immune response enhancers include adjuvants, biodegradable microspheres (e.g., polylactic galactide) and for example liposomes into which the polypeptide may be incorporated. Pharmaceutical compositions and vaccines may also contain other epitopes of tumor antigens, either incorporated into a fusion protein as described above (i.e., a single polypeptide that contains multiple epitopes) or present within a separate polypeptide.

Any suitable immune-response enhancer may be employed in the vaccines of this invention. For example, an adjuvant may be included. Most adjuvants contain a substance designed to protect the antigen from rapid catabolism, such as aluminium hydroxide or mineral oil, and a non-specific stimulator of immune response, such as lipid A, *Bordetella pertussis* or *Mycobacterium tuberculosis*. Such adjuvants are commercially available as, for example, Freund's Incomplete Adjuvant and Complete Adjuvant (Difco Laboratories, Detroit, Mich.) and Merck Adjuvant 65 (Merck and Company, Inc., Rahway, N.J.).

For therapeutic purposes polypeptides, polynucleotides or binding agents may be administered in a variety of ways. Possible ways may for example comprise intracutaneous, intramuscular, intravenous or subcutaneous injection, intranasal administration for example by aspiration or oral administration.

Another aspect of the present invention is to provide a method for therapy and/or vaccination. According to the present invention a therapy of cell proliferative disorders can be carried out using human transketolase like-1 polypeptides and/or polynucleotides. The therapy may be for example immunotherapy or somatic gene therapy.

The human transketolase like-1 polypeptides and/or polynucleotides may according to the present invention be used for vaccination against cell proliferative disorders. Vaccination according to the present invention may comprise administering an immunogenic compound to an individual for the purpose of stimulating an immune response directed against said immunogenic compound and thus immunizing said individual against said immunogenic compound. Stimulating an immune response may comprise inducing the production of antibodies against said compound as well as stimulating cytotoxic T-cells. For the purpose of vaccination the polypeptides, nucleic acids and binding agents according to the present invention may be administered in a physiological acceptable form. The composition to be administered to individuals may comprise one or more antigenic components, physiologically acceptable carrier substances or buffer solutions, immunostimulants and/or adjuvants. Adjuvants may comprise for example Freund's incomplete adjuvant or Freund's complete adjuvant or other adjuvants known to those of skill in the art.

The composition may be administered in any applicable way such as e.g. intravenous, subcutaneous, intramuscular etc. The dosage of the composition depends on the particular case and purpose of the vaccination. It has to be adapted to parameters by the individual treated such as age, weight, sex etc. Furthermore the type of the immune response to be elicited has to be taken into account. In general it may be preferable if an individual receives 100 μg-1 g of a polypeptide according to the present invention or $10^6$-$10^{12}$ MOI of a recombinant nucleic acid, containing a nucleic acid according to the present invention in a form that may be expressed in situ.

Individuals for the purpose of vaccination may be any organisms containing transketolase like-1 proteins and being able get affected by cell proliferative disorders.

Vaccination of individuals may be favourable e.g. in the case of altered, non wild-type sequences or structure of marker molecules associated with cell proliferative disorders.

Polypeptides disclosed herein may also be employed in adoptive immunotherapy for the treatment of cancer. Adoptive immunotherapy may be broadly classified into either active or passive immunotherapy. In active immunotherapy, treatment relies on the in vivo stimulation of the endogenous host immune system to react against tumors with the administration of immune response-modifying agents (for example, tumor vaccines, bacterial adjuvants, and/or cytokines).

In passive immunotherapy, treatment involves the delivery of biologic reagents with established tumor-immune reactivity (such as effector cells or antibodies) that can directly or indirectly mediate antitumor effects and does not necessarily depend on an intact host immune system. Examples of effector cells include T lymphocytes (for example, CD8+ cytotoxic T-lymphocyte, CD4+ T-helper, tumor-infiltrating lymphocytes), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage or B-cells, may be pulsed with immunoreactive polypeptides or transfected with a nucleic acid sequence(s), using standard techniques well known in the art. For example, antigen presenting cells may be transfected with a nucleic acid sequence, wherein said sequence contains a promoter region appropriate for increasing expression, and can be expressed as part of a recombinant virus or other expression system. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," Immunological Reviews, 157: 177, 1997).

The polypeptides disclosed herein may also be employed to generate and/or isolate tumor-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ CTL clones may be isolated from the patient, expanded using standard tissue culture techniques, and returned to the patient.

Alternatively, peptides corresponding to immunogenic portions of the polypeptides of the invention may be employed to generate tumor reactive T-cell subsets by selective in vitro stimulation and expansion of autologous T-cells to provide antigen-specific T-cells which may be subsequently transferred to the patient as described, for example, by Chang et al. (Crit. Rev. Oncol. Hematol., 22(3), 213, 1996). Cells of the immune system, such as T-cells, may be isolated from the peripheral blood of a patient, using a commercially available cell separation system, such as CellPro Incorporated's (Bothell, Wash.) CEPRATE™ system (see U.S. Pat. No. 5,240,856; U.S. Pat. No. 5,215,926; WO 89/06280; WO 91/16116 and WO 92/07243). The separated cells are stimulated with one or more of the immunoreactive polypeptides contained within a delivery vehicle, such as a microsphere, to provide antigen-specific T-cells. The population of tumor antigen-specific T-cells is then expanded using standard techniques and the cells are administered back to the patient.

In another embodiment, T-cell and/or antibody receptors specific for the polypeptides can be cloned, expanded, and transferred into other vectors or effector cells for use in adoptive immunotherapy.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T-cells to provide antigen-specific T-cells, which may, in turn, be administered to a patient. The use of peptide-pulsed dendritic cells to generate antigen-specific T-cells and the subsequent use of such antigen-specific T-cells to eradicate tumors in a murine model has been demonstrated by Cheever et al, Immunological Reviews, 157:177, 1997.

Additionally, vectors expressing the disclosed nucleic acids may be introduced into stem cells taken from the patient and clonally propagated in vitro for autologous transplant back into the same patient.

Monoclonal antibodies of the present invention may also be used as therapeutic compounds in order to diminish or eliminate tumors. The antibodies may be used on their own (for instance, to inhibit metastases) or coupled to one or more therapeutic agents. Suitable agents in this regard include radio nuclides, differentiation inducers, drugs, toxins, and derivatives thereof. Preferred radio nuclides include 90Y, 123I, 125I, 131I, 186Re, 188Re, 211At, and 212Bi. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, *Shigella* toxin, and pokeweed antiviral protein.

Furthermore methods for treatment of disorders associated with overexpression of transketolase like-1 gene may comprise any method suitable for the reduction of the activity of transketolase like 1 polypeptide in an individual or in cells of an individual. These methods may comprise a reduction of the activity of transketolase like-1 polypeptide by means of reduction of gene expression or by means of reduction of enzymatic activity. Examples may comprise the administration of antisense constructs, of ribozymes, of enzyme inhibitors, the administration of antagonists of cofactors of transketolase like-1 polypeptides, as e.g. antithiamine compounds or the reduced administration of essential cofactors for the enzymatic activity (e.g. thiamine).

The methods for administration of ribozymes or antisense constructs are known to those of skill in the art. The administration may take place as administration of naked nucleic acids or as administration of nucleic acids that are suited for expression of the relevant active products in situ.

In one preferred embodiment the therapy of disorders associated with the overexpression of transketolase like-1 gene comprises administration of antithiamine compounds, or the reduction of thiamine uptake for individuals showing disorders characterized by overexpression of transketolase like-1 gene.

In a further embodiment, the present invention relates to a method of identifying and obtaining a drug candidate for therapy of colon, stomach, pancreatic or lung tumors comprising the steps of contacting a TKT-L1 polypeptide as used in the method of the present invention or a cell expressing said polypeptide in the presence of components capable of providing a detectable signal in response to transketolase activity, to altered regulation of cell proliferation, and detecting presence or absence of a signal or increase of the signal generated from transketolase activity or altered regulation of cell proliferation, wherein the absence or decrease of the signal is indicative for a putative drug.

The drug candidate may be a single compound or a plurality of compounds. The term "plurality of compounds" in a method of the invention is to be understood as a plurality of substances which may or may not be identical.

Said compound or plurality of compounds may be chemically synthesized or microbiologically produced and/or comprised in, for example, samples, e.g., cell extracts from, e.g., plants, animals or microorganisms. Furthermore, said compound(s) may be known in the art but hitherto not known to be capable of suppressing or activating TKT-L1 polypeptides. The reaction mixture may be a cell free extract or may comprise a cell or tissue culture. Suitable set ups for the method of the invention are known to the person skilled in the art and are, for example, generally described in Alberts et al., Molecular Biology of the Cell, third edition (1994) and in the appended examples. The plurality of compounds may be, e.g., added to the reaction mixture, culture medium, injected into cell or otherwise applied to the transgenic animal. The cell or tissue that may be employed in the method of the invention preferably is a host cell, mammalian cell or non-human transgenic animal of the invention described in the embodiments hereinbefore.

If a sample containing a compound or a plurality of compounds is identified in the method of the invention, then it is either possible to isolate the compound from the original sample identified as containing the compound capable of suppressing or activating TKT-L1, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances of similar chemical and/or physical properties, and most preferably said substances are identical.

The compounds which can be tested and identified according to a method of the invention may be peptides, proteins, nucleic acids, antibodies, small organic compounds, hormones, peptidomimetics, PNAs or the like.

The compounds isolated by the above methods also serve as lead compounds for the development of analog compounds. The analogs should have a stabilized electronic configuration and molecular conformation that allows key functional groups to be presented to the TKT-L1 in substantially the same way as the lead compound. In particular, the analog compounds have spatial electronic properties which are comparable to the binding region, but can be smaller molecules than the lead compound, frequently having a molecular weight below about 2 kD and preferably below about 1 kD.

Identification of analog compounds can be performed through use of techniques such as self-consistent field (SCF) analysis, configuration interaction (CI) analysis, and normal mode dynamics analysis. Computer programs for implementing these techniques are available; e.g., Rein, Computer-Assisted Modeling of Receptor-Ligand Interactions (Alan Liss, New York, 1989). Methods for the preparation of chemical derivatives and analogues are well known to those skilled in the art and are described in, for example, Beilstein, Handbook of Organic Chemistry, Springer edition New York Inc., 175 Fifth Avenue, New York, N.Y. 10010 U.S.A. and Organic Synthesis, Wiley, N.Y., USA. Furthermore, said derivatives and analogues can be tested for their effects according to methods known in the art; see also supra. Furthermore, peptidomimetics and/or computer aided design of appropriate derivatives and analogues can be used, for example, according to the methods described above.

Once the described compound has been identified and obtained, it is preferably provided in a therapeutically acceptable form.

The present invention provides methods for detection and treatment of disorders characterized by abnormal cell proliferation, such as e.g. cancers. In one aspect the present invention provides a method for the detection of disorders characterized by abnormal cell proliferation, such as e.g. cancers based on the determination of the presence or absence and/or the level of expression of human transketolase like-1 gene in biological samples. In a second aspect the present invention provides a method for treatment of disorders characterized by abnormal cell proliferation, such as e.g. cancers using human transketolase like-1 gene products as therapeutically active agents. The invention also provides for therapeutic methods based on the reduction of the enzymatic activity of transketolase like-1 gene polypeptides. It is one aspect of the invention to provide a method for rational tumor management based on the detection of transketolase like-1 gene products in patient samples and the tailoring of a therapy correlated to the detected overexpression of said gene products. Furthermore the present invention provides for a research or diagnostic test kit for performing the reactions involved in the detection of the presence or absence and/or the level of overexpression of human transketolase like-1 gene. Finally the present invention relates to pharmaceutical compositions applicable in the treatment of disorders according to the present invention.

The following examples are given for the purpose of illustration only and are not intended to limit the scope of the invention disclosed herein.

EXAMPLE 1

Determining the Level of Human Transketolase Like-1 mRNA Levels in Colon Carcinoma Tissues Dissections of tumor biopsies can be semi-quantitatively analysed for the mRNA level of human transketolase like-1 gene in an in-situ staining reaction. The staining reaction is performed as follows:

The tissue dissections are incubated in ascending ethanol concentrations up to 100% ethanol. After evaporation of the alcohol the dissections are boiled in 10 mM citrate buffer (pH 6.0) for pre-treatment of the tissue. The hybridisation mixture is prepared by mixing 50 µl of ready to use hybridisation buffer (DAKO A/S, Glostrup, Danmark) with about 5-10 pmol of the probes. The probes are fluorescein-labelled oligonucleotides of the following sequence:

TCTCATCACAAGCAGCACAGGAC

The hybridisation mixture is heated to 95° C. and afterwards equilibrated to 37° C. After the boiling procedure the dissections are incubated with each 50 µl of the hybridisation mixture for 2 hours at 37° C. The dissections are washed in excess volumes of the wash buffers two times in 2×SSC at room temperature for 15 min and once in 1×SSC at 50° C. for 15 min Then the dissections are rinsed two times at room temperature in 2×SSC. Following this washing procedure the dissections are incubated for 30 min with blocking buffer (NEN, Blockingpugger) at room temperature. Then follows 1 hour incubation with a 1:100 diluted (in Blocking buffer, see above) Anti-Fluorescein-AP (DAKO A/S). The dissections are then washed 2 times in 1×PBS/0.1% Triton×100 for 10 min at room temperature, followed by one wash step with 1×PBS, 50 mM MgCl2 (pH 9.2) for 10 min at room temperature.

Then the staining reaction is performed with NBT/BCIP (Sigma) for about 30 min at room temperature. The staining reaction is stopped by a short incubation with 1 mM EDTA in PBS. Finally the dissections are dipped in $H_2O_{dest.}$ and fixed with AquaTex (Merck). Then the stained dissections can be analysed microscopically. The results show, that human transketolase like-1 gene is overexpressed in colon carcinoma tissue in comparison to normal colon tissue.

EXAMPLE 2

Determination of Human Transketolase Like-1 Gene and Transketolase Level in Tissues of Carcinomas and Control Tissues Using Semiquantitative RT PCR Samples of colon carcinoma, adenocarcinoma of the lung and of carcinomas of the stomach are used to determine the level of human transketolase like-1 mRNA and the level of human transketolase mRNA using semi-quantitative RT PCR. Tumor biopsies are used in this study.

Tumors are collected, snap frozen, and stored at −80° C. They are verified to be composed predominantly of neoplastic cells by histopathological analysis. mRNA is isolated from tumors and patient-matched normal tissue using Qiagen reagents (Qiagen, Hilden, Germany), and single-stranded cDNA is synthesized using Superscript II (Life Technologies, Inc.). Quantitative PCR is performed using the 7700 Sequence Detector (Taqman™) and the SYBR Green PCR Master-Mix, as described in the manufacturers manual (Applied Biosystems, Foster City, Calif.).

PCR reactions are performed in 25 µl volumes with a final concentration of 300 nmol for each primer, with 95° C. for 15 sec and 60° C. for 60 sec, for 40 cycles. The following primers are used for quantitative PCR:

```
Transketolase like-1:
Primer A: CACCTTGGGATTCTGTGTGC

Primer B: TCTCATCACAAGCAGCACAG

Transketolase:
Primer A: TGTGTCCAGTGCAGTAGTGG

Primer B: ACACTTCATACCCGCCCTAG
```

The specificity of the PCR products is verified by gel electrophoresis (data not shown).

The results show, that human transketolase like-1 gene is highly overexpressed in 1 out of 10 of colon carcinomas, in two out of five in lung adenocarcinomas and in three out of five carcinomas of the stomach in comparison to normal control tissue.

Especially the extent of overexpression of the transketolase like-1 gene in the samples is noticeable. In total six out of 20 carcinomas show more than eight fold overexpression of the TKT L-1 gene. In contrast the transketolase gene in no case is significantly overexpressed.

The result shows, that in a subset of cancers of different origins transketolase like-1 gene is overexpressed. The transketolase gene in contrast is not differentially expressed in the tested tumor tissue.

EXAMPLE 3

Immunochemical Detection of the Overexpression of tktl1 in Tissue Samples of Carcinomas Sections of formalin fixed, paraffin embedded gastric tissue samples were immunocytochemically stained using antibodies directed against tktl1.

The sections were rehydrated through incubation in xylene and graded ethanol, and transferred to Aqua bidest. Antigen Retrieval was carried out with 10 mM citrate buffer (pH 6.0) Therefore the slides were heated in a waterbath for 40 min at 95° C. The slides were cooled down to RT for 20 minutes, transferred to washing buffer (PBS/0.1% Tween20).

For inactivation of endogenous peroxidase the samples are incubated with 3% H2O2 for 10 min at RT and afterwards washed in PBS/0.1% Tween20 for 10 min.

The slides were then incubated with the primary antibody, mouse anti-tktl1 (1:300) (for 1 hour at RT, the slides were then rinsed with washing buffer and placed in a fresh buffer bath for 5 min. The antibody employed is directed against the protein sequence shown in bold in FIG. 7 of human tktl1.

Afterwards the slides were incubated with the secondary antibody (goat anti mouse (1:500)) for 1 hour at RT. Washing was performed 3 times for 5 minutes. Slides were covered with 200 µl substrate-chromogen solution (DAB) for 10 min. Then slides were washed as before and counterstained for 2 min in a bath of haematoxylin. Residual haematoxylin was rinsed with distilled water, and specimens were mounted and coverslipped with an aqueous mounting medium.

The microscopic examination of the slides reveals, that cells immunoreactive with tktl1 can be found in samples, that may microscopically be identified as samples of gastric carcinoma. In carcinomas the tktl1 specific staining is visible in the nucleus and the cytoplasm. In addition a granular staining pattern was observed in tumor cells.

The above described immunohistochemical staining procedure was furthermore applied to tissues from breast-, lung-, cervical- (CINIII), gastric-, oesophageal-, endometrial-, ovarian-carcinomas. In all these cases nuclear and cytoplasmic staining for tktl1 could be observed in the cancerous cells.

Moreover metastases from colorectal carcinoma located in the liver were analysed by immunochemical procedures as described above. The result showed a strong overexpression of the tktl1 protein.

The invention claimed is:

1. An in vitro method for detection of carcinoma in an individual comprising:
   (a) obtaining a suspected carcinoma sample from an individual;
   (b) detecting in the sample obtained from said individual the level of transketolase like-1 polypeptide encoded by transketolase like-1 gene;
   (c) comparing the level detected in step (b) with the level of transketolase like-1 polypeptide encoded by a transketolase like-1 gene in a corresponding control non-carcinoma sample from a healthy subject; and
   (d) in the case that the sample from the individual has a higher level of transketolase like-1 polypeptide encoded by a transketolase like-1 gene than the control tissue sample, diagnosing said sample as indicative of a carcinoma.

2. The method according to claim 1, wherein the carcinoma is colon cancer, lung cancer, gastric cancer, pancreatic cancer, cervical cancer, breast cancer, or bladder cancer.

3. The method according to claim 1, wherein in step (b) the detection is carried out by using an antibody directed against transketolase like-1 protein.

4. The method according to claim 1, wherein in step (b) the detection is carried out by using a delectably labeled protein detecting probe.

5. The method according to claim 4, wherein the label is selected from the group consisting of a radioisotope, a bioluminescent compound, a chemiluminescent compound, a fluorescent compound, a metal chelate, and a enzyme suitable to detect proteins.

6. The method according to claim 1, wherein step (b) comprises performing in vitro molecular imaging.

7. The method according to claim 1, wherein said transketolase-like 1 gene is as given in NCBI Accession No. X 91817.

8. An in vitro method for detection of carcinoma in an individual comprising:
   (a) obtaining a suspected carcinoma sample from an individual;
   (b) detecting in the sample obtained from said individual the level of polypeptide encoded by polynucleotide having the nucleic acid sequence of SEQ ID NO: 1;
   (c) comparing the level detected in step (b) with the level of polypeptide encoded by polynucleotide having the nucleic acid sequence of SEQ ID NO:1 in a corresponding control non-carcinoma sample from a healthy subject; and
   (d) in the case that the sample from the individual has a higher level of polypeptide encoded by polynucleotides having the nucleic acid sequence of SEQ ID NO:1 than the control tissue sample, diagnosing said sample as indicative of a carcinoma.

9. The method according to claim 8, wherein the carcinoma is colon cancer, lung cancer, gastric cancer, pancreatic cancer, cervical cancer, breast cancer, or bladder cancer.

10. The method according to claim 8, wherein in step (b) the detection is carried out by using an antibody directed against transketolase like-1 protein.

11. The method according to claim 8, wherein in step (b) the detection is carried out by using a detectably labeled protein detecting probe.

12. The method according to claim 11, wherein the label is selected from the group consisting of a radioisotope, a bioluminescent compound, a chemiluminescent compound, a fluorescent compound, a metal chelate, and a enzyme suitable to detect proteins.

13. The method according to claim 8, wherein step (b) comprises performing in vitro molecular imaging.

14. An in vitro method for detection of carcinoma in an individual comprising:
   (a) obtaining a biological tissue sample suspected to contain cancerous cells from an individual;
   (b) detecting in said biological tissue sample obtained from said individual the level of transketolase like-1 polypeptide encoded by transketolase like-1 gene;
   (c) comparing the results of step (b) with a reference value obtained by detecting, in a normal control sample of the same type as the suspected cancerous biological tissue sample but known to be non-cancerous, the level of transketolase like-1 polypeptide encoded by a transketolase like-1 gene; and
   (d) in the case that a higher level of transketolase like-1 polypeptide is detected in said suspected cancerous biological tissue sample suspected to contain cancerous cells as compared to said level of transketolase like-1 polypeptide in said normal control sample, diagnosing said individual as having a carcinoma.

15. The method according to claim 14, wherein the carcinoma is colon cancer, lung cancer, gastric cancer, pancreatic cancer, cervical cancer, breast cancer, or bladder cancer.

16. The method according to claim 14, wherein in step (b) the detection is carried out by using an antibody directed against transketolase like-1 protein.

17. The method according to claim 14, wherein in step (b) the detection is carried out by using a detectably labeled protein detecting probe.

18. The method according to claim 17, wherein the label is selected from the group consisting of a radioisotope, a bioluminescent compound, a chemiluminescent compound, a fluorescent compound, a metal chelate, and a enzyme suitable to detect proteins.

19. The method according to claim 1, wherein step (b) comprises performing in vitro molecular imaging.

20. The method according to claim 1, wherein said transketolase-like 1 gene is as given in NCBI Accession No. X 91817.

21. An in vitro method for detection of carcinoma in an individual comprising:
(a) obtaining a biological tissue sample suspected to contain cancerous cells from an individual;
(b) detecting in said biological tissue sample obtained from said individual the level of polypeptide comprising the amino acid sequence encoded by polynucleotides having the nucleic acid sequence of SEQ ID NO: 1;
(c) comparing the results of step (b) with a reference value obtained by detecting, in a normal control sample of the same type as the suspected cancerous biological tissue sample but known to be non-cancerous, the level of polypeptide comprising the amino acid sequence encoded by polynucleotides having the nucleic acid sequence of SEQ ID NO:1; and
(d) in the case that a higher level of polypeptides is detected in said suspected cancerous biological tissue sample suspected to contain cancerous cells as compared to said level of polypeptides in said normal control sample, diagnosing said individual as having a carcinoma.

22. The method according to claim 21, wherein the carcinoma is colon cancer, lung cancer, gastric cancer, pancreatic cancer, cervical cancer, breast cancer, or bladder cancer.

23. The method according to claim 21, wherein in step (b) the detection is carried out by using an antibody directed against transketolase like-1 protein.

24. The method according to claim 21, wherein in step (b) the detection is carried out by using a detectably labeled protein detecting probe.

25. The method according to claim 24, wherein the label is selected from the group consisting of a radioisotope, a bioluminescent compound, a chemiluminescent compound, a fluorescent compound, a metal chelate, and a enzyme suitable to detect proteins.

26. The method according to claim 21, wherein step (b) comprises performing in vitro molecular imaging.

27. An in vitro method for detection of carcinoma in an individual comprising:
(a) obtaining a biological test sample from an individual suspected to be suffering of carcinoma, said test sample being selected from the group consisting of serum, blood, plasma, urine, semen, stool, bile, a biopsy or a cell- or tissue-sample, gastric juice, and pancreatic juice;
(b) detecting in said biological test sample obtained from said individual the level of transketolase like-1 polypeptide encoded by transketolase like-1 gene;
(c) comparing the results of step (b) with a reference value obtained by detecting, in a normal control sample of the same type and, in the case of tissue, of the same tissue type, as the test sample but known to be non-cancerous, the level of transketolase like 1 polypeptide encoded by the transketolase like-1 gene; and
(d) in the case that a higher level of transketolase like 1 polypeptide is detected in said biological test sample as compared to said level of transketolase like 1 polypeptide in said normal control sample, diagnosing said individual as having a carcinoma.

28. The method according to claim 27, wherein the carcinoma is colon cancer, lung cancer, gastric cancer, pancreatic cancer, cervical cancer, breast cancer, or bladder cancer.

29. The method according to claim 27, wherein in step (b) the detection is carried out by using an antibody directed against transketolase like-1 protein.

30. The method according to claim 27, wherein in step (b) the detection is carried out by using a detectably labeled protein detecting probe.

31. The method according to claim 30, wherein the label is selected from the group consisting of a radioisotope, a bioluminescent compound, a chemiluminescent compound, a fluorescent compound, a metal chelate, and a enzyme suitable to detect proteins.

32. The method according to claim 27, wherein step (b) comprises performing in vitro molecular imaging.

33. The method according to claim 27, wherein said transketolase-like 1 gene is as given in NCBI Accession No. X 91817.

34. An in vitro method for detection of carcinoma in an individual comprising:
(a) obtaining a biological test sample from an individual suspected to be suffering of carcinoma, said test sample being selected from the group consisting of serum, blood, plasma, urine, semen, stool, bile, a biopsy or a cell- or tissue-sample, gastric juice, and pancreatic juice;
(b) detecting in said biological test sample obtained from said individual the level of polypeptide encoded by polynucleotides having the nucleic acid sequence of SEQ ID NO:1;
(c) comparing the results of step (b) with a reference value obtained by detecting, in a normal control sample of the same type and, in the case of tissue, of the same tissue type, as the test sample but known to be non-cancerous, the level of polypeptide encoded by polynucleotides having the nucleic acid sequence of SEQ ID NO:1; and
(d) in the case that a higher level of polypeptides is detected in said biological test sample as compared to said level of polypeptides in said normal control sample, diagnosing said individual as having a carcinoma.

35. The method according to claim 34, wherein the carcinoma is colon cancer, lung cancer, gastric cancer, pancreatic cancer, cervical cancer, breast cancer, or bladder cancer.

36. The method according to claim 34, wherein in step (b) the detection is carried out by using an antibody directed against transketolase like-1 protein.

37. The method according to claim 34, wherein in step (b) the detection is carried out by using a detectably labeled protein detecting probe.

38. The method according to claim 37, wherein the label is selected from the group consisting of a radioisotope, a bioluminescent compound, a chemiluminescent compound, a fluorescent compound, a metal chelate, and a enzyme suitable to detect proteins.

39. The method according to claim 34, wherein step (b) comprises performing in vitro molecular imaging.

40. The method according to claim 1, wherein the carcinoma sample is a cancerous biological tissue sample.

41. The method according to claim 8, wherein the carcinoma sample is a cancerous biological tissue sample.

* * * * *

SEQUENCE LISTING

<160> NUMBER OF SEQ ID NOS: 9

<210> SEQ ID NO 1
<211> LENGTH: 2531
<212> TYPE: DNA
<213> ORGANISM: Homo sapiens

<400> SEQUENCE: 1

```
gccattcgct cttcagacgc cggagacgta ggagtgggtc ttcagactcc aaaggggttg        60
gactaatggc ggatgctgag gcgagggctg agttcccgga ggaggccaga cctgacaggg       120
gcaccttgca ggtgttgcaa gatatggcca gccgcttgcg aatccattcc atcagggcca       180
catgctccac gagctccggc caccctacat catgtagcag ttcttctgag atcatgtctg       240
tgctgttctt ctacatcatg aggtacaagc agtcagatcc agagaatccg gacaacgacc       300
gatttgtcct cgcaaagaga ctgtcgtttg tggatgtggc aacaggatgg ctcggacaag       360
gactgggagt tgcatgtgga atggcatata ctggcaagta cttcgacagg gccagctacc       420
gggtgttctg cctcatgagt gatggcgagt cctcagaagg ctctgtctgg gaggcaatgg       480
cctttgcttc ctactacagt ctggacaatc ttgtgcaat ctttgatgtg aaccgcctgg       540
gacacagtgg tgcattgccc gccgagcact gcataaacat ctatcagagg cgctgcgaag       600
cctttgggtg gaacacttat gtggtggacg gccgggacgt ggaggcactg tgccaggtat       660
tctggcaggc ttctcaggtg aagcacaagc ccactgctgt ggtggccaag accttcaagg       720
gccgggcac cccaagtatt gaggatgcag aaagttggca tgcaaagcca atgccgagag       780
aaagagcaga tgccattatc aaattaattg agaccagat acagaccagc aggaatcttg       840
acccacagcc ccccattgag gactcacctg aagtcaacat cacagatgta aggatgacct       900
ctccacctga ttacagagtt ggtgacaaga tagctactcg gaaagcatgc ggtctggctc       960
tggctaagct gggctacgcg aacaacagag tcgttgtgct ggatggtgac accaggtact      1020
ctactttctc tgagatattc aacaaggagt accctgagcg cttcatcgag tgctttatgg      1080
ctgaacaaaa catggtgagc gtggctctgg gctgtgcctc ccgtgacgg accattgctt      1140
ttgctagcac ctttgctgcc tttctgactc gagcatttga tcacatccgg ataggaggcc      1200
tcgctgagag caacatcaac attattggtt cccactgtgg ggtatctgtt ggtgacgatg      1260
gtgcttccca gatggccctg gaggatatag ccatgttccg aaccattccc aagtgcacga      1320
tcttctaccc aactgatgcc gtctccacgg agcatgctgt tgctctggca gccaatgcca      1380
aggggatgtg cttcattcgg accacccgac cagaaactat ggttatttac accccacaag      1440
aacgctttga gatcggacag gccaaggtcc tccgccactg tgtcagtgac aaggtcacag      1500
ttattggagc tggaattact gtgtatgaag ccttagcagc tgctgatgag ctttcgaaac      1560
aagatatttt tatccgtgtc atcgacctgt ttaccattaa acctctggat gtcgccacca      1620
tcgtctccag tgcaaaagcc acagagggcc ggatcattac agtggaggat cactacccgc      1680
aagtggcat cggggaagct gtctgcgcag ccgtctccat ggatcctgac attcaggttc      1740
attcgctggc agtgtcggga gtgccccaga gtgggaagtc cgaggaattg ctggatatgt      1800
atggaattag tgccagacat atcatagtgg ccgtgaaatg catgttgctg aactaaaata      1860
gctgttagcc ttggtctttt ggcctcttta ccctgtgttt atgtttgttc caaaaccatc      1920
atttaaatct ctactgtcac attttgtttc ttaaaagcaa agccagctaa caccttcatt      1980
catccctagt tcggaaattc aagctaacta cttacccttt aaactgtcac tgcatatgca      2040
```

```
agtaccgctc taattttttgg atcattaaag ggagttacac aacttttaag tgaaaaaaat    2100
aggtaacaaa acaaccacct gatagtaagt tttctgataa gactatagat aagtggtaga    2160
ggtaatcaat tcttccgaag tgtttccttc gtgaataact ggtagaggta atagtttttt    2220
caatgtattt ccttcatgag taaagaaaat gtggattgaa gtatagattc cagtagccta    2280
gtttccacag cacgataaca ccatgacgcc tactgctgtt cccaccttgg gattctgtgt    2340
gctgccatcc cacctgcagc tgccctggaa ttcccttcgc tgtttgcctt catctccctc    2400
cacgtttgag aggctgtcag gcagcagcga aagcttgtta ggatgtcctg tgctgcttgt    2460
gatgagagcc tccacactgt actgttcaag tcaatgttaa taaagcattt caaaaccaaa    2520
aaaaaaaaaa a                                                        2531
```

<210> SEQ ID NO 2
<211> LENGTH: 596
<212> TYPE: PRT
<213> ORGANISM: Homo sapiens

<400> SEQUENCE: 2

```
Met Ala Asp Ala Glu Ala Arg Ala Glu Phe Pro Glu Glu Ala Arg Pro
1               5                   10                  15

Asp Arg Gly Thr Leu Gln Val Leu Gln Asp Met Ala Ser Arg Leu Arg
            20                  25                  30

Ile His Ser Ile Arg Ala Thr Cys Ser Thr Ser Ser Gly His Pro Thr
        35                  40                  45

Ser Cys Ser Ser Ser Ser Glu Ile Met Ser Val Leu Phe Phe Tyr Ile
    50                  55                  60

Met Arg Tyr Lys Gln Ser Asp Pro Glu Asn Pro Asp Asn Asp Arg Phe
65                  70                  75                  80

Val Leu Ala Lys Arg Leu Ser Phe Val Asp Val Ala Thr Gly Trp Leu
                85                  90                  95

Gly Gln Gly Leu Gly Val Ala Cys Gly Met Ala Tyr Thr Gly Lys Tyr
            100                 105                 110

Phe Asp Arg Ala Ser Tyr Arg Val Phe Cys Leu Met Ser Asp Gly Glu
        115                 120                 125

Ser Ser Glu Gly Ser Val Trp Glu Ala Met Ala Phe Ala Ser Tyr Tyr
    130                 135                 140

Ser Leu Asp Asn Leu Val Ala Ile Phe Asp Val Asn Arg Leu Gly His
145                 150                 155                 160

Ser Gly Ala Leu Pro Ala Glu His Cys Ile Asn Ile Tyr Gln Arg Arg
                165                 170                 175

Cys Glu Ala Phe Gly Trp Asn Thr Tyr Val Val Asp Gly Arg Asp Val
            180                 185                 190

Glu Ala Leu Cys Gln Val Phe Trp Gln Ala Ser Gln Val Lys His Lys
        195                 200                 205

Pro Thr Ala Val Val Ala Lys Thr Phe Lys Gly Arg Gly Thr Pro Ser
    210                 215                 220

Ile Glu Asp Ala Glu Ser Trp His Ala Lys Pro Met Pro Arg Glu Arg
225                 230                 235                 240

Ala Asp Ala Ile Ile Lys Leu Ile Glu Ser Gln Ile Gln Thr Ser Arg
                245                 250                 255

Asn Leu Asp Pro Gln Pro Pro Ile Glu Asp Ser Pro Glu Val Asn Ile
            260                 265                 270

Thr Asp Val Arg Met Thr Ser Pro Pro Asp Tyr Arg Val Gly Asp Lys
        275                 280                 285
```

```
Ile Ala Thr Arg Lys Ala Cys Gly Leu Ala Leu Ala Lys Leu Gly Tyr
    290                 295                 300

Ala Asn Asn Arg Val Val Leu Asp Gly Asp Thr Arg Tyr Ser Thr
305                 310                 315                 320

Phe Ser Glu Ile Phe Asn Lys Glu Tyr Pro Glu Arg Phe Ile Glu Cys
                325                 330                 335

Phe Met Ala Glu Gln Asn Met Val Ser Val Ala Leu Gly Cys Ala Ser
                340                 345                 350

Arg Gly Arg Thr Ile Ala Phe Ala Ser Thr Phe Ala Ala Phe Leu Thr
                355                 360                 365

Arg Ala Phe Asp His Ile Arg Ile Gly Leu Ala Glu Ser Asn Ile
370                 375                 380

Asn Ile Ile Gly Ser His Cys Gly Val Ser Val Gly Asp Asp Gly Ala
385                 390                 395                 400

Ser Gln Met Ala Leu Glu Asp Ile Ala Met Phe Arg Thr Ile Pro Lys
                405                 410                 415

Cys Thr Ile Phe Tyr Pro Thr Asp Ala Val Ser Thr Glu His Ala Val
                420                 425                 430

Ala Leu Ala Ala Asn Ala Lys Gly Met Cys Phe Ile Arg Thr Thr Arg
                435                 440                 445

Pro Glu Thr Met Val Ile Tyr Thr Pro Gln Glu Arg Phe Glu Ile Gly
    450                 455                 460

Gln Ala Lys Val Leu Arg His Cys Val Ser Asp Lys Val Thr Val Ile
465                 470                 475                 480

Gly Ala Gly Ile Thr Val Tyr Glu Ala Leu Ala Ala Asp Glu Leu
                485                 490                 495

Ser Lys Gln Asp Ile Phe Ile Arg Val Ile Asp Leu Phe Thr Ile Lys
                500                 505                 510

Pro Leu Asp Val Ala Thr Ile Val Ser Ser Ala Lys Ala Thr Glu Gly
                515                 520                 525

Arg Ile Ile Thr Val Glu Asp His Tyr Pro Gln Gly Gly Ile Gly Glu
    530                 535                 540

Ala Val Cys Ala Ala Val Ser Met Asp Pro Asp Ile Gln Val His Ser
545                 550                 555                 560

Leu Ala Val Ser Gly Val Pro Gln Ser Gly Lys Ser Glu Glu Leu Leu
                565                 570                 575

Asp Met Tyr Gly Ile Ser Ala Arg His Ile Ile Val Ala Val Lys Cys
                580                 585                 590

Met Leu Leu Asn
        595

<210> SEQ ID NO 3
<211> LENGTH: 213
<212> TYPE: PRT
<213> ORGANISM: Homo sapiens

<400> SEQUENCE: 3

Ser Gly Ala Leu Pro Ala Glu His Cys Ile Asn Ile Tyr Gln Arg Arg
1               5                   10                  15

Cys Glu Ala Phe Gly Trp Asn Thr Tyr Val Val Asp Gly Arg Asp Val
                20                  25                  30

Glu Ala Leu Cys Gln Val Phe Trp Gln Ala Ser Gln Val Lys His Lys
                35                  40                  45

Pro Thr Ala Val Val Ala Lys Thr Phe Lys Gly Arg Gly Thr Pro Ser
    50                  55                  60
```

```
Ile Glu Asp Ala Glu Ser Trp His Ala Lys Pro Met Pro Arg Glu Arg
 65                 70                  75                  80

Ala Asp Ala Ile Ile Lys Leu Ile Glu Ser Gln Ile Gln Thr Ser Arg
             85                  90                  95

Asn Leu Asp Pro Gln Pro Pro Ile Glu Asp Ser Pro Glu Val Asn Ile
            100                 105                 110

Thr Asp Val Arg Met Thr Ser Pro Pro Asp Tyr Arg Val Gly Asp Lys
        115                 120                 125

Ile Ala Thr Arg Lys Ala Cys Gly Leu Ala Leu Ala Lys Leu Gly Tyr
    130                 135                 140

Ala Asn Asn Arg Val Val Val Leu Asp Gly Asp Thr Arg Tyr Ser Thr
145                 150                 155                 160

Phe Ser Glu Ile Phe Asn Lys Glu Tyr Pro Glu Arg Phe Ile Glu Cys
                165                 170                 175

Phe Met Ala Glu Gln Asn Met Val Ser Val Ala Leu Gly Cys Ala Ser
            180                 185                 190

Arg Gly Arg Thr Ile Ala Phe Ala Ser Thr Phe Ala Ala Phe Leu Thr
        195                 200                 205

Arg Ala Phe Asp His
    210

<210> SEQ ID NO 4
<211> LENGTH: 17
<212> TYPE: PRT
<213> ORGANISM: Homo sapiens

<400> SEQUENCE: 4

Ser Arg Asn Leu Asp Pro Gln Pro Pro Ile Glu Asp Ser Pro Glu Val
1               5                  10                  15

Asn

<210> SEQ ID NO 5
<211> LENGTH: 15
<212> TYPE: PRT
<213> ORGANISM: Homo sapiens

<400> SEQUENCE: 5

Tyr Ala Asn Asn Arg Val Val Val Leu Asp Gly Asp Thr Arg Tyr
1               5                  10                  15

<210> SEQ ID NO 6
<211> LENGTH: 20
<212> TYPE: DNA
<213> ORGANISM: Homo sapiens

<400> SEQUENCE: 6
caccttggga ttctgtgtgc                                              20

<210> SEQ ID NO 7
<211> LENGTH: 20
<212> TYPE: DNA
<213> ORGANISM: Homo sapiens

<400> SEQUENCE: 7
tctcatcaca agcagcacag                                              20

<210> SEQ ID NO 8
<211> LENGTH: 20
<212> TYPE: DNA
<213> ORGANISM: Homo sapiens
```

```
<400> SEQUENCE: 8
tgtgtccagt gcagtagtgg                                                        20

<210> SEQ ID NO 9
<211> LENGTH: 20
<212> TYPE: DNA
<213> ORGANISM: Homo sapiens

<400> SEQUENCE: 9
acacttcata cccgccctag                                                        20
```